United States Patent [19]
Gidda et al.

[11] Patent Number: 5,096,908
[45] Date of Patent: Mar. 17, 1992

[54] METHOD OF INHIBITING GASTRIC ACID SECRETION

[75] Inventors: Jaswant S. Gidda, Carmel; John M. Schaus, Zionsville, both of Ind.

[73] Assignee: Eli Lilly and Company, Indianapolis, Ind.

[21] Appl. No.: 519,388

[22] Filed: May 4, 1990

[51] Int. Cl.$^5$ .............................................. A61K 31/47
[52] U.S. Cl. ...................................................... 514/307
[58] Field of Search ......................................... 514/307

[56] References Cited

U.S. PATENT DOCUMENTS

| | | | |
|---|---|---|---|
| 2,906,757 | 9/1959 | Mills et al. | 549/366 |
| 2,922,744 | 1/1960 | Mills et al. | 514/452 |
| 3,551,493 | 12/1970 | Ruschig et al. | 654/338 |
| 4,576,959 | 3/1986 | Flaugh | 514/411 |
| 4,745,126 | 5/1988 | Leander | 514/411 |
| 4,818,756 | 4/1989 | Seidel et al. | 514/224.2 |
| 4,845,221 | 7/1989 | Stack et al. | 544/295 |
| 4,885,302 | 12/1989 | George et al. | 514/307 |

FOREIGN PATENT DOCUMENTS

| | | |
|---|---|---|
| 082402 | 6/1983 | European Pat. Off. |
| 148440 | 7/1985 | European Pat. Off. |
| 153083 | 8/1985 | European Pat. Off. |
| 170213 | 2/1986 | European Pat. Off. |
| 272534 | 6/1988 | European Pat. Off. |
| 306375 | 3/1989 | European Pat. Off. |
| 334538 | 9/1989 | European Pat. Off. |
| 345056 | 12/1989 | European Pat. Off. |

OTHER PUBLICATIONS

Chemical Abstracts (110:231451d) 1989.
Glennon, R. A., *J. Med. Chem.*, 30, 1–12 (1987).
*Handbook of Experimental Pharmacology*, vol. XIX, "5-Hydroxytryptamine and Related Indolealkylamines", Erspamer, V. sub-ed, Springer-Verlog, New York, 1966, pp. 329–335.
Bulbring, E. et al., *Adv. Pharmac.*, 6A, 323–333 (1968).
Blundell, J. E., *Neuropharmacology*, 23, 1537–1551 (1984).
Arvidsson, L. E. et al., *J. Med. Chem.*, 27, 45–51 (1984).
Naiman, N. et al., *J. Med. Chem.*, 32, 253–256 (1989).
Arvidsson, L. E. et al., *J. Med. Chem.*, 24, 921–923 (1981).
Middlemiss, D. N. et al., *Annu. Rep. Med. Chem.*, 21, 41–50 (1986).
Fuller, R. W., *Monogr. Neural Sci.*, 10, 158–181 (1984).
Taylor, E. W. et al., *Mol. Pharmacol.*, 34, 42–53 (1988).
Nelson, W. L. et al., *J. Med. Chem.*, 20, 880–885 (1977).
Augstein, J. et al., *J. Med. Chem.*, 8, 446–456 (1965).
Hibert, M. T. et al., *J. Med. Chem.*, 31, 1087–1093 (1988).
Arvidsson, L. E. et al., *J. Med. Chem.*, 31, 92–99 (1988).
Wu, Y. H. et al., *J. Med. Chem.*, 15, 477–479 (1972).
Yevich, J. P. et al., *J. Med. Chem.*, 26, 194–203 (1983).
Gharbia, M. et al., *J. Med. Chem.*, 31, 1382–1392 (1988).
Wu, Y. H. et al., *J. Med. Chem.*, 12, 876–881 (1969).
Glennon, R. A. et al., *J. Med. Chem.*, 31, 867–870 (1988).

*Primary Examiner*—Frederick G. Waddell
*Assistant Examiner*—K. Weddington
*Attorney, Agent, or Firm*—John C. Demeter; Leroy Whitaker

[57] ABSTRACT

The present invention provides a method of inhibiting gastric acid secretion in mammals by administering a 5-HT1A agonist compound or a pharmaceutically acceptable salt thereof.

4 Claims, No Drawings

METHOD OF INHIBITING GASTRIC ACID SECRETION

BACKGROUND OF THE INVENTION

Over the last several years it has become apparent that serotonin (5-hydroxytryptamine; 5-HT) is associated directly or indirectly with a number of physiological phenomena, including appetite, memory, thermoregulation, sleep, sexual behavior, anxiety, depression, and hallucinogenic behavior [Glennon, R. A., *J. Med. Chem.* 30, 1 (1987)].

5-HT receptors have been identified in the central nervous system (CNS; brain and spinal cord) and in peripheral tissues including the gastrointestinal tract, lung, heart, blood vessels, and various other smooth muscle tissues.

It has been recognized that there are multiple types of 5-HT receptors. These receptors have been classified as 5-HT1, 5-HT2, and 5-HT3 with at least the 5-HT1 receptor being further divided into sub-classes identified as 5-HT1A, 5-HT1B, 5-HT1C, and 5-HT1D.

In the CNS, 5-HT receptors are located post-synaptically, on neurons that receive serotonergic input, and presynaptically on 5-HT releasing neurons. The presynaptic receptors are believed to function to sense the concentration of 5-HT in the synaptic cleft and modulate the further release of 5-HT accordingly.

Generally, an "agonist" is a chemical compound that mimics the action of the endogenous neurotransmitter at receptors.

Direct-acting serotonin agonists are chemical substances that bind to and mimic the action of serotonin on serotonin receptors.

Indirect-acting serotonin agonists are chemical substances that increase the concentration of serotonin in the synaptic cleft. Indirect serotonin agonists include inhibitors of a serotonin specific uptake carrier, agents that release serotonin from storage granules, agents (serotonin precursors) that increase serotonin formation, and monoamine oxidase (MAO) inhibitors that block serotonin degradation and thereby increase the amount of serotonin available.

The primary focus of research efforts surrounding the biochemistry and physiology of serotonin and serotonin agonists has been directed toward the CNS, generally, and the brain in particular.

Serotonin is known to have a number of actions in the gastrointestinal tract. It is known that the intravenous infusion in humans of 5-HT or 5-HTP (5-hydroxytryptophane) inhibits the volume and acidity of both spontaneous and histamine induced gastric secretion while simultaneously increasing the production of mucus [*Handbook of Experimental Pharmacology*, Vol XIX, "5-Hydroxytryptamine and Related Indolealkylamines" Erspamer, V., sub-ed., Springer-Verlog, New York, 1966, pp. 329-335]. It is not known whether binding at one or some combination of 5-HT receptor sites is required to effect this inhibition response or which receptor(s) are involved.

It is known that 5-HT receptors in smooth muscle of the gastrointestinal tract mediate contraction of this tissue. The rat fundus and guinea pig ileum are widely used for in vitro studies of 5-HT agonists and antagonists. The enterochromaffin cells of the gastrointestinal tract are the major site of 5-HT production in the body. Although 5-HT and 5-HT receptors are known to be present in the gastrointestinal tract, their physiological roles are not clear.

It has been discovered that direct acting 5-HT1A agonists inhibit the secretion of gastric acid. These agents are, therefore, useful in the treatment of conditions where inhibition of gastric acid secretion is necessary or desirable such as gastric and peptic ulceration.

It is a primary object of the present invention to provide a method of inhibiting gastric acid secretion by administering to a mammal in need of such treatment a compound having direct-acting 5-HT1A receptor agonist activity.

Other objects, features and advantages of the present invention will become apparent to one skilled in the art from the subsequent description and the appended claims.

SUMMARY OF THE INVENTION

The present invention provides a method of inhibiting gastric acid secretion in mammals comprising administering to a mammal in need of gastric acid secretion inhibition an effective dose of a direct acting 5-HT1A receptor agonist or a pharmaceutically acceptable salt thereof.

DETAILED DESCRIPTION OF THE INVENTION

The method of this invention is practiced by administering to a mammal a direct acting 5-HT1A agonist or a pharmaceutically acceptable salt thereof, preferably in a pharmaceutical formulation.

The phrase "direct acting 5-HT1A agonist" as used in this specification and these claims means a non-endogenous chemical compound and includes: 1) synthetic chemical compounds (ligands) that mimic the action of serotonin on 5-HT1A receptors by directly activating these receptors; and 2) partial agonists, which are synthetic chemical compounds (ligands) that mimic the action of serotonin on 5-HT1A receptors by directly activating these receptors but produce a smaller maximal effect than do other ligands that act on the same receptor. These compounds may have activity at other receptors but must have some component of 5-HT1A agonist activity.

Compounds within both of these groups of ligands must possess both affinity for the 5-HT1A receptor site and efficacy in that gastric acid secretion is lowered. The affinity and efficacy may be at CNS receptors, peripheral receptors or both or on acid secretory cell receptors; that is, the compounds within either group may be able to pass the blood/brain barrier, but this is not a requirement.

The 5-HT1A agonists contemplated as within the scope of the present invention are those having an apparent binding affinity, typically reported as $K_i$ value, of from about 0.01 nM to about 5000 nM calculated from inhibitor $IC_{50}$ values using the equation $K_i = IC_{50}/[1+(L/K_d)]$ where L is the radioligand concentration and $K_d$ is the dissociation constant of the ligand-receptor complex determined by saturation studies or from the inhibition by the cold ligand for its own binding.

Procedures for performing binding assays to determine 5-HT1A agonist activity are known to those skilled in the art. For example, such techniques are described in Wong et al., *Life Sciences*, 46, 231-235 (1990) and references cited therein. Similarly, the relationship between apparent binding affinity $K_i$ as a function of inhibitor $IC_{50}$ values, radioligand concentration and dissociation of the ligand-receptor complex as described in the above formula is also known to those skilled in the art. For example, see Cheng et. al., *Biochemical Pharmacology*, 22, 3099-3108 (1973); and Taylor et. al., *Life Sciences*, 41, 1961-1969 (1987).

The method of the present invention is useful in the treatment and prevention of disorders of the gastrointestinal tract associated with unnecessary or undesirable gastric acid secretion including peptic ulcer gastric and duodenal ulcers, gastritis, gastroesophogeal reflux disease, gastric dispepsia, and Zollinger-Ellison syndrome.

The following classes of direct acting 5-HT1A agonists have been reported and are useful in the method of the present invention: 1) 2-amino-1,2,3,4-tetrahydronaphthalenes and 3-amino chromanes; 2) 4-amino-1,3,4,5-tetrahydrobenz-[c,d]indoles; 3) nonendogenous indoles; 4) aryloxy propanolamines; 5) benzodioxanes; 6) phenylcyclopropylamines; 7) N-arylpiperazines; and 8) piperidinylmethyl tetrahydroisoquinolines. Each of these classes will now be described in further detail.

2-Amino-1,2,3,4-Tetrahydronaphthalenes and 3-Amino Chromanes

The first class comprises 8-substituted-2-amino-1,2,3,4-tetrahydronaphthalenes, and the corresponding 5-substituted-3-amino chromanes, having 5-HT1A agonist activity, and pharmaceutically acceptable acid addition salts thereof. The 2-amino-1,2,3,4-tetrahydronaphthalenes are more widely known with 8-hydroxy-2-dipropylamino-1,2,3,4-tetrahydronaphthalene (8-OH-DPAT) as perhaps the best known example. Further tetrahydronaphthalene analogues include the 8-methoxy derivative and 2-mono-($C_1$-$C_4$)alkylamino and di($C_1$-$C_4$)alkylamino derivatives. These compounds and others are described in and prepared according to procedures in Arvidsson, L. E. et al., *J. Med. Chem.*, 27, 45 (1984); Naiman, N. et al., *J. Med. Chem.*, 32, 253 (1989); EPA 334 538, U.S. Pat. No. 4,845,221; and EPA 272 534A which are all incorporated herein by reference in their entirety. Specific illustrative compounds include:

8-methoxy-2-(methylamino)-1,2,3,4-tetrahydronaphthalene
8-hydroxy-2-(methylamino)-1,2,3,4-tetrahydronaphthalene
8-methoxy-2-(ethylamino)-1,2,3,4-tetrahydronaphthalene
8-hydroxy-2-(ethylamino)-1,2,3,4-tetrahydronaphthalene
(±) 8-methoxy-2-(propylamino)-1,2,3,4-tetrahydronaphthalene
(+) 8-methoxy-2-(propylamino)-1,2,3,4-tetrahydronaphthalene
(−) 8-methoxy-2-(propylamino)-1,2,3,4-tetrahydronaphthalene
8-hydroxy-2-(propylamino)-1,2,3,4-tetrahydronaphthalene
8-methoxy-2-(butylamino)-1,2,3,4-tetrahydronaphthalene
8-hydroxy-2-(butylamino)-1,2,3,4-tetrahydronaphthalene
8-methoxy-2-(isopropylamino)-1,2,3,4-tetrahydronaphthalene
8-hydroxy-2-(isopropylamino)-1,2,3,4-tetrahydronaphthalene
8-methoxy-2-(dimethylamino)-1,2,3,4-tetrahydronaphthalene
8-hydroxy-2-(dimethylamino)-1,2,3,4-tetrahydronaphthalene
8-methoxy-2-(diethylamino)-1,2,3,4-tetrahydronaphthalene
8-hydroxy-2-(diethylamino)-1,2,3,4-tetrahydronaphthalene
8-methoxy-2-(ethylpropylamino)-1,2,3,4-tetrahydronaphthalene
8-hydroxy-2(ethylpropylamino)-1,2,3,4-tetrahydronaphthalene
(±) 8-methoxy-2-(dipropylamino)-1,2,3,4-tetrahydronaphthalene
(+) 8-methoxy-2-(dipropylamino)-1,2,3,4-tetrahydronaphthalene
(−) 8-methoxy-2-(dipropylamino)-1,2,3,4-tetrahydronaphthalene
(±) 8-OH-DPAT
(+) 8-OH-DPAT
(−) 8-OH-DPAT
8-methoxy-2-(propylbutylamino)-1,2,3,4-tetrahydronaphthalene
8-hydroxy-2-(propylbutylamino)-1,2,3,4-tetrahydronaphthalene Additional ring-substituted 2-amino-1,2,3,4-tetrahydronaphthalenes and 3-amino chromanes having 5-HT1A agonist activity, are those having the formula

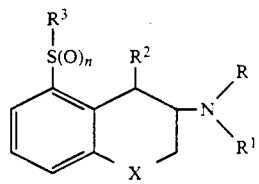

in which
R is $C_1$-$C_4$ alkyl, allyl, or cyclopropylmethyl;
$R^1$ is hydrogen, $C_1$-$C_4$ alkyl, allyl, cyclopropylmethyl, or aryl($C_1$-$C_4$ -alkyl);
$R^2$ is hydrogen or methyl;
X is —$CH_2$— or —O—;
$R^3$ is $C_1$-$C_8$ alkyl, aryl, substituted aryl, aryl($C_1$-$C_4$-alkyl), substituted aryl($C_1$-$C_4$ alkyl), or $C_5$-$C_7$; cycloalkyl:
n is 0, 1, or 2;
and pharmaceutically acceptable acid addition salts thereof.

In the above formula, the term "$C_1$-$C_4$ alkyl" means a straight or branched alkyl chain having from one to four carbon atoms. Such $C_1$-$C_4$ alkyl groups are methyl, ethyl, n-propyl, isopropyl, n-butyl, isobutyl, sec-butyl, and t-butyl.

The term "aryl" means an aromatic structure whether carbocyclic or heterocyclic. Examples of such ring structures are phenyl, naphthyl, furyl, pyridyl, thienyl, and the like.

The aryl group may contain a ring substituent. Examples of typical ring substituents are $C_1$-$C_3$ alkyl, $C_1$-$C_3$ alkoxy, halo, hydroxy, $C_1$-$C_3$ thioalkyl, trifluoromethyl, and the like.

In the foregoing, the term "$C_1$-$C_3$ alkoxy" means any of methoxy, ethoxy, n-propoxy, and isopropoxy; the term "halo" means any of fluoro, chloro, bromo, and iodo; and the term "$C_1$-$C_3$ thioalkyl" means any of methylthio, ethylthio, n-propylthio, and isopropylthio.

Among the 5-HT1A agonist compounds included in this class as described above, including those compounds described in references that have been incorporated by reference, certain of these compounds are preferred. The preferred compounds are those having the Formula ID

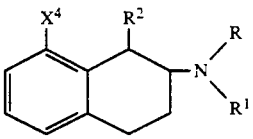

where
R is $C_1$-$C_4$ alkyl, allyl, or ($C_3$-$C_5$ alkyl)methyl;
$R^1$ is hydrogen, $C_1$-$C_4$ alkyl; allyl; ($C_3$-$C_5$ cycloalkyl)-methyl, or aryl($C_1$-$C_4$ -alkyl);
$R^2$ is hydrogen or methyl;
$X^4$ is OH, $C_1$-$C_6$ alkoxy, halo, $COOR^3$ or $S(O)_nR^3$;
$R^3$ is $C_1$-$C_8$ alkyl, aryl, substituted aryl, aryl($C_1$-$C_4$-alkyl), substituted aryl($C_1$-$C_4$ alkyl); or $C_5$-$C_7$ cycloalkyl; or
R and $R^1$ together with the nitrogen atom form a group

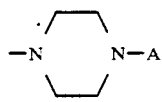

where A is
3-trifluoromethylphenyl, 3-halophenyl,
2-pyrimidinyl, halopyrimidin-2-yl,
2-pyrazinyl or halo-2-pyrazinyl;
n is 0, 1, or 2; or a pharmaceutically acceptable acid addition salt thereof.

More preferably, $R^2$ is hydrogen; R and $R^1$ preferably are both $C_1$-$C_4$ alkyl, and, more preferably, both are n-propyl. Also, n preferably is zero; $R^3$ preferably is $C_1$-$C_8$ alkyl, substituted aryl, or substituted aryl($C_1$-$C_4$-alkyl), and, most preferably, methyl.

The compounds of Formula I and other 2-amino-1,2,3,4-tetrahydronaphthalenes within class one possess an asymmetric carbon represented by the carbon atom labeled with an asterisk in the following formula:

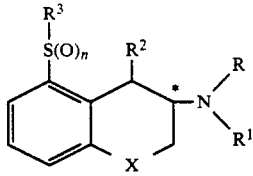

As such, each of the compounds exists as its individual d- and l-stereoisomers as well as the racemic mixture of such isomers. Accordingly, the compounds of the present invention include not only the dl-racemates but also their respective optically active d- and l-isomers.

In addition, when $R^2$ is methyl, a second asymmetric carbon, at the $R^2$ substituent, is present, giving rise to a further class of stereoisomers.

As mentioned hereinabove, useful compounds for practicing the method of the present invention includes pharmaceutically acceptable acid addition salts of the compounds defined by the above Formula I and other 2-amino-1,2,3,4-tetrahydronaphthalenes within class one. Since these compounds are amines, they are basic in nature and accordingly react with any of a number of inorganic and organic acids to form pharmaceutically acceptable acid addition salts. Since the free amines of these compounds are typically oils at room temperature, it is preferable to convert the free amines to their corresponding pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene2-sulfonate, mandelate, and the like. Preferred pharmaceutically acceptable acid addition salts are those formed with mineral acids such as hydrochloric acid and hydrobromic acid, and those formed with organic acids such as maleic acid.

In addition, some of these salts may form solvates with water or organic solvents such as ethanol. Such solvates also are included within the scope of this invention.

The following compounds further illustrate compounds contemplated within the scope of Formula I:
1-Methyl-2-(di-n-propylamino)-8-methylthio-1,2,3,4-tetrahydronaphthalene;
2-Ethylamino-8-ethylthio-1,2,3,4-tetrahydronaphthalene;
2-(N-Methyl-N-benzylamino)-8-methylthio-1,2,3,4-tetrahydronaphthalene;
2-Diallylamino-8-ethylthio-1,2,3,4-tetrahydronaphthalene;
1-Methyl-2-diethylamino-8-ethylsulfinyl-1,2,3,4-tetrahydronaphthalene;
1-Methyl-2-(di-n-propylamino)-8-ethanesulfonyl-1,2,3,4-tetrahydronaphthalene;
1-Methyl-2-benzylmethylamino-8-methylthio-1,2,3,4-tetrahydronaphthalene;
1-Methyl-2-(di-n-propylamino)-8-n-propylthio-1,2,3,4-tetrahydronaphthalene;
2-Dimethylamino-8-benzenesulfonyl-1,2,3,4-tetrahydronaphthalene;
2-(Di-cyclopropylmethylamino)-8-(p-toluenesulfonyl)-1,2,3,4-tetrahydronaphthalene;
2-(Di-n-propylamino)-8-(p-chlorobenzenesulfonyl)-thio-1,2,3,4-tetrahydronaphthalene;
2-Ethylamino-8-n-propylthio-1,2,3,4-tetrahydronaphthalene;
2-n-Butylamino-8-ethylthio-1,2,3,4-tetrahydronaphthalene;
2-(Di-n-propylamino)-8-n-octylthio-1,2,3,4-tetrahydronaphthalene;

2-(Di-n-propylamino)-8-methylthio-1,2,3,4-tetrahydronaphthalene;

3-(Di-n-propylamino)-5-methylthio-chromane; and the like.

The compounds of Formula I may be prepared by procedures well known to those of ordinary skill in the art. The compounds in which X is —CH$_2$ preferably are synthesized by preparation of an 8-bromo-2-tetralone. The 8-bromo-2-tetralone then is reductively aminated with the desired amine after which the bromo substituent is replaced with the desired thio substituent.

Schemes for these reactions are as follows:

tetralone. The 8-bromo-2-tetralone first is treated with pyrrolidine to produce the corresponding 1,2-dihydro-3-pyrrolidinyl-naphthalene. The latter, upon treatment with methyl iodide and acid hydrolysis, gives the desired 8-bromo-1-methyl-2-tetralone.

The tetralone, once formed, can, by simple reductive amination using the selected amine, be converted to a 2-amino-8-bromo-1,2,3,4-tetrahydronaphthalene useful as an intermediate to a compound of Formula I. The tetralone is first reacted with the amine to form the corresponding enamine after which the enamine is reduced with sodium borohydride or sodium cyanoboro- A. Synthesis of 8-Bromo-2-tetralone and 8-Bromo-1-methyl-2-tetralone

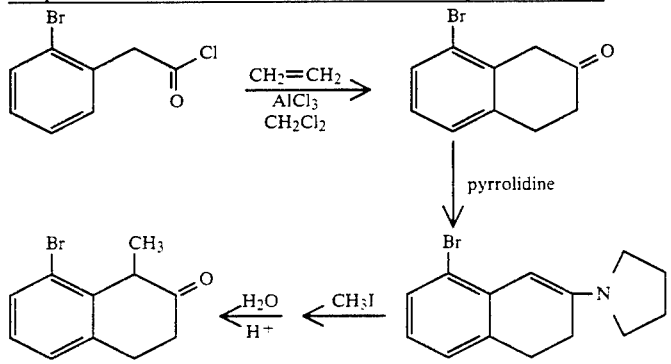

B. Reductive Amination

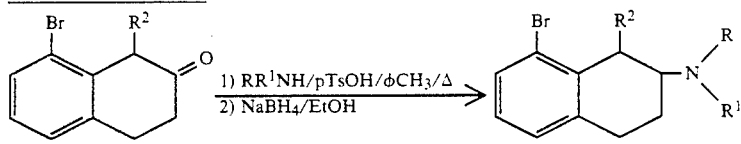

C. Replacement of Bromo Ring Substituent Via Lithiation

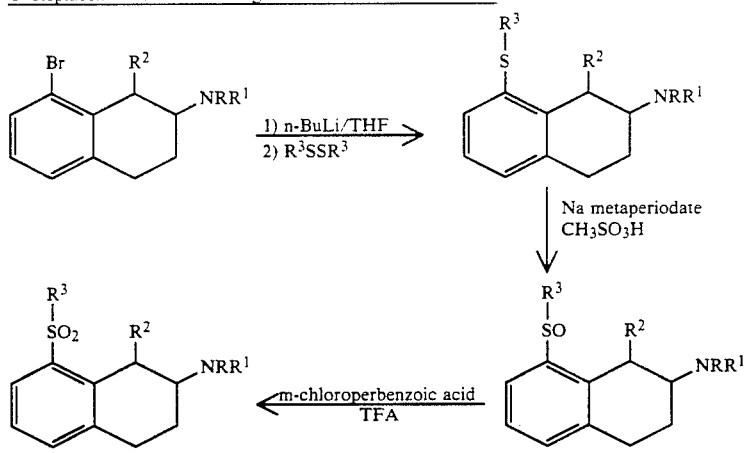

As depicted above, the 8-bromo-2-tetralones represent the intermediate which, when reductiely aminated, lithiated, and treated with the appropriate disulfide, result in compounds of Formula I and/or compounds useful as intermediates to the preparation of compounds of Formula I.

The tetralones are available by any of a wide range of recognized methods. For example, they can be produced by a Friedel-Crafts reaction of an appropriately ring-substituted phenylacetyl chloride with ethylene in the presence of aluminum chloride.

When R$^2$ in the compounds of Formula I is methyl, the methyl-substituted 8-bromo-2-tetralone can be prepared from the corresponding unsubstituted 8-bromo-2- hydride to the tetrahydronaphthalene.

The 2-amino-8-bromo-1,2,3,4-tetrahydronaphthalene is used to produce compounds of Formula I by formation of a lithium intermediate via a lithiation reaction using an alkyl lithium, preferably n-butyllithium. The reactive lithium intermediate then is treated with an appropriate disulfide to produce the 8-thio compounds of Formula I.

Alternatively, the 8-bromo-2-tetralone can first be protected and then lithiated and treated with the appropriate disulfide. The resulting 8-thio-2-tetralone, after deprotection, can then be reductively aminated to a compound of Formula I.

The compounds of Formula I in which X is oxygen are available by reductive amination and bromo replacement as in the foregoing, but using 5-bromo-3-chromanone. This molecule can be produced by a sequence of reactions beginning with m-bromophenol. The detailed reaction sequence is provided in the Examples following. Briefly, m-bromophenol is treated with allyl bromide in the presence of potassium carbonate to produce allyl 3-bromophenyl ether. The ether is converted to 2-allyl-3-bromophenol upon heating it in the presence of N,N-dimethylaniline. The phenol, upon reaction with ethyl chloroacetate, is converted to the ethyl ester of 2-allyl-3-(carboxymethoxy)bromobenzene. Upon oxidation using ozone followed by reductive work up, the allyl group is converted to a formylmethyl substituent which is then further oxidized using Jones' Reagent to the carboxymethyl substituent, the resulting product being the ethyl ester of (2-carboxymethyl-3-bromo)phenoxyacetic acid. The partial ester is converted to the diethyl ester using ethanol and gaseous hydrogen chloride. In the presence of potassium t-butoxide, the diester is cyclized to a mixture of 4-ethoxycarbonyl-5-bromo-3-chromanone and 2-ethoxycarbonyl-5-bromo-3-chromanone. Upon heating the latter in the presence of acid, it is converted to 5-bromo-3-chromanone.

The 8-thio compounds, upon treatment with sodium metaperiodate, can be oxidized to the corresponding 8-sulfinyl compounds. Additional compounds, the 8-sulfonyl compounds, are available by treatment of the 8-sulfinyl compounds with n-chloroperbenzoic acid.

The optically active isomers of the racemates of the invention are also considered within the scope of Formula I. Such optically active isomers may be prepared from their respective optically active precursors by the procedures described above, or by resolving the racemic mixtures. These resolutions can can typically be carried out in the presence of a resolving agent, by chromatography or by repeated crystallization. Procedures for separating racemates into their individual isomers can be found in references such as Jacques et. al, *Enantiomers, Racemates and Resolutions*, (John Wiley and Sons, New York 1981). This reference describes procedures used to find a resolving agent using the trial and error method. It also describes how to carry out a resolution after finding a resolving agent.

As described above, the compounds of Formula I generally and conveniently are produced via an 8-substituted-2-tetralone or a 5-substituted-3-chromanone. Either of these intermediates may be reductively alkylated with an optically active α-phenethylamine after which the resulting mixture of diastereomers is separated by recognized methodology, such as chromatography. Cleavage of the α-phenethyl moiety produces a correspondingly substituted, optically active 2-amino-1,2,3,4-tetrahydronaphthalene or 3-aminochromane.

The conditions necessary for removing the phenethyl moiety are relatively severe and can cleave substituent groups on the core tetralin or chromane molecule. The cleavage of the phenethyl moiety can be carried out in a much more facile and efficient manner requiring only mild cleavage conditions when the particular α-phenethylamin which is used is p-nitro-α-phenethylamine.

Cleavage of the p-nitro-α-phenethyl moiety is achieved by reduction of the p-nitro group followed by acid-catalyzed solvolysis of the resulting p-amino-α-phenethyl moiety. Reduction of the nitro group can be accomplished by a wide range of reducing agents including, for example, titanium trichloride, or zinc/acetic acid, or by catalytic hydrogenation particularly using sulfided palladium on carbon as catalyst. Solvolytic cleavage takes place when the monohydrochloride (or other monobasic salt) of the reduction product is teeated with water or an alcohol at room temperature or, in some instances, at elevated temperatures. A particularly convenient condition for removing the p-nitro-α-phenethyl moiety is hydrogenation of the amine monohydrochloride in methanol over a platinum catalyst.

Compounds highly useful as intermediates to the compounds of Formula I are the corresponding 8-bromotetralins. It has been discovered that the 8-bromo compounds in their optically active form are not available using routine methodology. The optical antipodes of 8-bromo-2-aminotetralin may be prepared using methods employing p-nitro-α-phenethylamine described above. These compounds may then be converted to compounds IB and IC using alkylating procedures known to those skilled in the art.

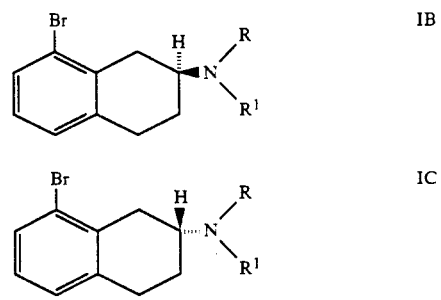

In the foregoing, R is hydrogen, $C_1$–$C_4$ alkyl, allyl, or cyclopropylmethyl; and $R^1$ is hydrogen, $C_1$–$C_4$ alkyl, allyl, cyclopropylmethyl, or aryl($C_1$–$C_4$-alkyl).

The compounds employed as initial starting materials in the synthesis of the compounds of this invention are well known and readily synthesized by standard procedures commonly employed by those of ordinary skill in the art.

The pharmaceutically acceptable acid addition salts are typically formed by reacting a 1,2,3,4-tetrahydronaphthalene or chromane of Formula I with an equimolar or excess amount of acid. The reactants are generally combined in a mutual solvent such as diethyl ether or benzene, and the salt normally precipitates out of solution within about one hour to 10 days, and can be isolated by filtration.

The following preparation Examples further illustrate the compounds of Formula I and methods for their synthesis. These Examples are not intended to be limiting to the scope of the invention in any respect and should not be so construed.

Unless otherwise noted, the NMR data appearing in the following examples refers to the free bases of the subject compounds.

PREPARATION EXAMPLE 1

Preparation of
2-Di-n-propylamino-8-thiomethyl-1,2,3,4-tetrahydronaphthalene.

A.
2-Di-n-propylamino-8-bromo-1,2,3,4-tetrahydronaphthalene.

To a solution of 8-bromo-2-tetralone (3.0 gm, 13.3 mMol) in toluene (25 mL) were added di-n-propylamine (3.5 mL, 26 mMol) and p-toluenesulfonic acid (100 mg, 0.52 mMol). The reaction was heated to reflux, water being collected in a Dean-Stark trap. After four hours the reaction was concentrated in vacuo to give 8-bromo-2-dipropylamino-3,4-dihydronaphthalene as a dark liquid which was immediately dissolved in methanol (50 mL) and acetic acid (5 mL). To this solution was then added sodium borohydride (2.0 gm, 52.9 mMol), and the mixture was stirred 18 hours at room temperature.

The reaction mixture was then diluted with 6N hydrochloric acid, stirred one hour at room temperature and then concentrated in vacuo. The residue was dissolved in water and washed once with diethyl ether. The remaining aqueous phase was made strongly basic with ammonium hydroxide and extracted well with dichloromethane. These organics were combined, dried ($Na_2SO_4$) and concentrated in vacuo to give the crude title compound as a dark oil. Purification by chromatography on basic alumina (dichloromethane) gave the product as a colorless oil. The hydrochloride salt was formed. Recrystallization (ethanol/diethyl ether) gave a colorless, crystalline solid (1.30 gm, 28%, m.p. = 155° C.).

Alternatively, to the 8-bromo-2-dipropylamino-3,4-dihydronaphthalene (44.4 mMol) in tetrahydrofuran (100 ml) was added sodium cyano-borohydride (2.86 gm, 45.5 mMol) and the suspension was saturated with hydrogen chloride. After stirring for four hours the reaction mixture was poured into 15% aqueous sodium hydroxide (500 ml) and was stirred an additional two hours. This mixture was extracted with diethyl ether, and the ether extracts were combined, washed with water, washed with saturated aqueous sodium chloride, dried ($Na_2SO_4$) and concentrated in vacuo to give the crude title compound as a light orange oil. Purification by basic alumina chromatography (dichloromethane) gave the product as a light yellow oil (7.8 gm, 57%).

Analysis: Calculated for $C_{16}H_{24}NBr.HCl$: Theory: C, 55.42; H, 7.27; N, 4.04; Found: C, 5.53; H, 7.22; N, 3.84.

MS: 311(17), 309(16), 282(100), 280(100), 211(30), 209(32), 130(92), 129(54), 128(40), 115(32), 72(43).

NMR ($CDCl_3$) 7.6–7.25(m, 1H), 7.2–6.9(m, 2H), 3.35–2.80(m, 5H), 2.80–2.40(m, 4H), 2.40–1.20(m, 6H), 1.19–0.80(t, J=7 Hz, 6H).

B.
2-Di-n-propylamino-8-methylthio-1,2,3,4-tetrahydronaphthalene

To a solution of 8-bromo-2-di-n-propylamino-1,2,3,4-tetrahydronaphthalene (600 mg, 1.93 mMol) in tetrahydrofuran (20 mL) at −78° C. was added a solution of n-butyllithium in hexane (1.6 M, 1.9 mL, 3.04 mMol). The solution was stirred at −78° C. for one hour, forming a light orange solution. Dimethyl disulfide (0.24 mL, 3.00 mMol) was added, and the reaction mixture was allowed to warm gradually to room temperature. The colorless solution was diluted with water and extracted with dichloromethane. The dichloromethane extracts were combined, dried ($Na_2SO_4$), and concentrated in vacuo to give the crude product as a light yellow oil. Purification by flash chromatography (3% methanol in dichloromethane + tr. $NH_4OH$) gave the product as a colorless, viscous oil (430 mg, 80%). The hydrochloride salt was formed. Recrystallization (ethanol/diethyl ether) gave a colorless, crystalline solid (m.p. = 185° C.).

Analysis: Calculated for $C_{17}H_{27}NS.HCl$ Theory: C, 65.04; H, 8.99; N, 4.46; Found: C, 65.25; H, 9.13; N, 4.47.

MS: 277(31), 251(10), 250(29), 248(100), 177(90), 132(15), 130(69), 128(50), 127(48).

NMR ($CDCl_3$): 7.13–6.68(m, 3H), 3.20–2.68(m, 4H), 2.62–2.33(m, 4H), 2.44(s, 3H), 2.12–1.81(m, 1H), 1.72–1.20(m, 6H), 1.00–0.86 (6, J=7 Hz, 6H).

PREPARATION EXAMPLE 2

Preparation of
2-Di-n-propylamino-8-thioethyl-1,2,3,4-tetrahydronaphthalene

Using the procedure described in Example 1, 8-bromo-2-di-n-propylamino-1,2,3,4-tetrahydronaphthalene (930 mg, 3.0 mMol) was reacted with diethyl disulfide (0.40 mL, 3.3 mMol) to give the crude title compound as a light yellow oil. Purification by flash chromatography (33% diethyl ether in hexane + tr. $NH_4OH$) gave the desired product as a colorless oil (650 mg, 74%). The fumarate salt was formed. Recrystallization (ethanol/-diethyl ether) gave a colorless, crystalline solid (m.p. = 105°–107° C.). Analysis Calculated for $C_{18}H_{29}NS.C_4H_4O_4$:

Theory: C, 62.09; H, 8.28; N, 2.83; Found: C, 61.87; H, 8.42; N, 3.11.

MS: 292(3), 290(16), 281(2), 280(8), 278(29), 250(18), 249(11), 207(5), 134(26), 119(10), 74(56), 59(88), 44(78).

NMR ($CDCl_3$): 7.08–6.72(m, 3H), 3.24–2.70(m, 6H), 2.70–2.36(m, 4H), 2.16–1.86(m, 1H), 1.76–1.20(m, 9H), 1.08–0.76(t, J=7 Hz, 6H).

PREPARATION EXAMPLE 3

Preparation of
2-Di-n-propylamino-8-thiophenyl-1,2,3,4-tetrahydronaphthalene

Using the procedure described in Example 1, 8-bromo-2-di-n-propylamino-1,2,3,4-tetrahydronaphthalene (930 mg, 3.0 mMol) was reacted with diphenyl disulfide (720 mg, 3.3 mMol) to give the title compound as a colorless oil. The fumarate salt was formed. Recrystallization (acetone/diethyl ether) gave colorless crystals (270 mg, 20%, m.p. = 133–135° C.).

Analysis: Calculated for $C_{22}H_{29}Ns.C_4H_4O_4$: Theory: C, 68.54; H, 7.30; N, 3.07; Found: C, 68.37; H, 7.24; N, 3.09.

MS: 339(16), 311(7), 310(25), 309(100), 239(24), 237(22), 161(28), 130(35), 129(40), 128(35).

NMR ($CDCl_3$): 7.18(s, 5H), 7.04–6.80(m, 3H), 3.08–2.72(m, 4H), 2.32–2.27(m, 4H), 2.11–1.63(m, 1H), 1.63–1.18(m, 6H), 1.04–0.68(t, J=7 Hz, 3H).

PREPARATION EXAMPLE 4

Preparation of
2-Di-n-propylamino-8-thiobenzyl-1,2,3,4-tetrahydronaphthalene.

Using the procedure described in Example 1, 8-bromo-2-di-n-propylamino-1,2,3,4-tetrahydronaphthalene (930 mg, 3.0 mMol) was reacted with dibenzyl disulfide (840 mg, 3.3 mMol) to give the crude title compound as a light yellow oil. Purification by flash chromatography (3% methanol in dichloromethane+tr. NH$_4$OH) gave the desired product as a colorless oil (630 mg, 60%). The maleate salt was formed. Recrystallization (ethanol/-diethyl ether) gave a colorless, crystalline solid (m.p.=137°–138.5° C.).

Analysis: Calculated for C$_{23}$H$_{31}$NS.C$_4$H$_4$O$_4$: Theory: C, 69.05 H, 7.51; N, 2.98; Found: C, 69.28; H, 7.47; N, 2.86.

MS: 353(10), 325(17), 324(63), 262(21), 253(8), 203(10), 161(10), 129(25), 127(19), 91(100).

NMR (CDCl$_3$): 7.32–6.68(m, 8H), 4.06(s, 2H), 3.16–2.62(m, 4H), 2.62–2.24(m, 4H), 2.16–1.80(m, 1H), 1.71–1.18(m, 6H), 1.08–0.72(t, J=7 Hz, 6H).

PREPARATION EXAMPLE 5

Preparation of 2-Di-n-propylamino-8-methylsulfinyl-1,2,3,4-tetrahydronaphthalene To a solution of water (60 mL) which contains methanesulfonic acid (0.16 mL, 2.33 mMol) was added 2-dipropylamino-8-methylthio-1,2,3,4-tetrahydronaphthalene (630 mg, 2.33 mMol). To this solution was added a solution of sodium metaperiodate (550 mg, 2.57 mMol) in water (10 mL), and the reaction mixture was stirred for two days at room temperature. The reaction mixture was made basic (NH$_4$OH) and extracted with dichloromethane. The organic extracts were combined, dried (Na$_2$SO$_4$) and concentrated in vacuo to give the crude title compound as a light yellow oil. Purification by flash chromatography (3% methanol in dichloromethane+tr. NH$_4$OH) gave the desired product (580 mg, 85%) as a colorless oil. The fumarate salt was formed. Recrystallization (ethanol/diethyl ether) gave a colorless, crystalline solid which was found to be extremely hygroscopic. Drying in a vacuum dessicator (60° C., 18 hours) gave a colorless glass (260 mg, m.p.=63° C.).

Analysis: Calculated for C$_{17}$H$_{27}$NOS.C$_4$H$_4$O$_4$: Theory: C, 61.59; H, 7.63; N, 3.42; Found: C, 61.38; H, 7.48; N, 3.57.

MS: 294(3), 293(4), 291(1), 278(10), 277(14), 276(60), 266(12), 265(33), 264(100), 250(7), 249(28), 248(8), 193(46).

NMR (CDCl$_3$): 7.80–7.76(m, 1H), 7.36–7.00(m, 2H), 3.28–2.20(m, 8H), 2.76–2.62(d, J=3 Hz, 3H), 2.20–1.85(m, 1H), 1.80–1.20(m, 6H), 1.04–0.72(t, J=7 Hz, 6H).

PREPARATION EXAMPLE 6

Preparation of 2-Di-n-propylamino-8-methylsulfonyl-1,2,3,4-tetrahydronaphthalene To a solution of 2-dipropylamino-8-methylsulfinyl-1,2,3,4-tetrahydronaphthalene (350 mg, 1.19 mMol) in trifluoroacetic acid (20 ml) was added a solution of metachloroperbenzoic acid (80%, 518 mg, 2.38 mMol) in trifluoroacetic acid (5 mL). The solution was stirred at room temperature for 18 hours and poured over ice. The resulting mixture was made basic (NH$_4$OH) and extracted well with dichloromethane. The organic extracts were combined, dried (Na$_2$SO$_4$) and concentrated in vacuo to give the crude title compound as a brown oil. Purification by flash chromatography (3% methanol in dichloromethane+tr. NH$_4$OH) gave the desired product as a light orange oil (110 mg, 30%). The maleate salt was formed. Recrystallization (ethanol/-diethyl ether) gave a colorless solid (70 mg, m.p.=113°–114° C.).

Analysis: Calculated for C$_{17}$H$_{27}$NO$_2$S.C$_4$H$_4$O$_4$: Theory: C, 59.27; H, 7.34; N, 3.29; Found: C, 59.19; H, 7.35; N, 3.18.

MS: 309(3), 283(1), 282(8), 281(18), 280(100), 209(11), 130(45).

NMR (CDCl$_3$): 7.88–7.76(dd, J=3 Hz, 7 Hz, 1H), 7.36–7.12(m, 2H), 3.20–2.78(m, 4H), 3.08(s, 3H), 2.64–2.38(m, 4H), 2.20–1.84(m, 1H), 1.80–1.14(m, 6H), 1.08–0.86(t, J=7 Hz, 6H).

PREPARATION EXAMPLE 7

Preparation of 2-Dimethylamino-8-thiomethyl-1,2,3,4-tetrahydronaphthalene

A.

2-Dimethylamino-8-bromo-1,2,3,4-tetrahydronaphthalene

To a solution of 8-bromo-2-tetralone (4.5 gm, mMol) in acetonitrile (100 mL) were added sodium acetate (9.9 gm, 120 mMol), sodium cyanoborohydride (880 mg, 120 mMol), dimethylamine hydrochloride (9.8 gm, mMol) and 4A sieves (2.0 gm). The mixture was stirred at room temperature for 3 days. The reaction mixture was then filtered through a bed of celite, and the filtrate was poured into a slurry of ice and water. The solution was made acidic (HCl) and extracted well with diethyl ether. The remaining aqueous was made basic (NH$_4$OH) and extracted well with dichloromethane. These organic phases were combined, dried (Na$_2$SO$_4$), and concentrated in vacuo to give a dark oil. Purification by flash chromatography (5% methanol in dichloromethane+tr. NH$_4$OH) gave the title compound as a yellow oil (1.5 gm, 30%).

MS: 257(2), 256(10), 255(42), 254(18), 253(42), 252(8), 240(7), 238(8), 174(13), 130(18), 129(40), 128(24), 115(20), 103(21), 84(43), 71(100), 70(68).

NMR (CDCl$_3$): 7.55–7.18(m, 1H), 7.16–6.85(m, 2H), 3.2–2.43(m, 6H), 2.4(s, 6H), 2.0–1.8(m, 1H).

B.

2-Dimethylamino-8-thiomethyl-1,2,3,4-tetrahydronaphthalene

To a solution of 2-Dimethylamino-8-bromo-1,2,3,4-tetrahydronaphthalene (760 mg, 3 mMol) in tetrahydrofuran (20 mL) at −78° C. was added n-butyllithium in hexane (1.6 M, 3.0 mL, 4.8 mMol). The solution was stirred at −78° C. for one hour. To the solution was then added dimethyl disulfide (0.33 mL, 4.1 mMol), and the resulting mixture was allowed to warm to room temperature. The light yellow solution was diluted with water, made acidic (HCl), and extracted well with diethyl ether. The remaining aqueous was made basic (NH$_4$OH) and extracted well with dichloromethane. These organics were combined, dried (Na$_2$SO$_4$), and concentrated in vacuo to give a light yellow oil. Purification by flash chromatography (3% methanol in dichloromethane+tr. NH$_4$OH) gave the desired compound as a light yellow oil (420 mg, 63%). The hydrochloride salt was formed. Recrystallization (acetone/-diethyl ether) gave a colorless, crystalline solid (m.p.=170° C.).

Analysis: Calculated for C$_{13}$H$_{19}$NS.HCl: Theory: C, 60.56; H, 7.82; N, 5.43; Found: C, 60.87; H, 7.94; N, 5.43.

MS: 223(4), 222(10), 221(100), 220(6), 219(1), 206(9), 177(33), 71(52).

NMR (CDCl₃): 7.2-6.8(m, 3H), 3.05-2.48(m, 5H), 2.45(s, 3H), 2.40(s, 6H), 2.15-2.00(m, 1H), 1.7-1.5(m, 1H).

PREPARATION EXAMPLE 8

Preparation of cis-1-Methyl-2-di-n-propylamino-8-thiomethyl-1,2,3,4-tetrahydronaphthalene

A. 1-Methyl-8-bromo-2-tetralone

To a solution of 8-bromo-2-tetralone (10 gm, 44.4 mMol) in toluene (175 ml) was added pyrrolidine (6.6 ml), and the solution was stirred at reflux for three hours. The volatiles were removed in vacuo to give 8-bromo-3-pyrrolidino-1,2-dihydronaphthalene as a brown oil. To this oil in p-dioxane (60 mL) was added methyl iodide (20 mL, 322 mMol), and the resulting solution was stirred at reflux for eighteen hours. The reaction mixture was diluted with water (60 mL) and acetic acid (3.2 mL), and heating was continued for an additonal three hours. After this time the solution was cooled to room temperature and the volatiles removed in vacuo. The residue was suspended in water and extracted well with diethyl ether. The organic phases were combined, washed with saturated aqueous NaHCO₃, dried with Na₂SO₄ and concentrated in vacuo to give an orange oil. Purification by flash chromatography (33% diethyl ether in hexane) gave the title compound as a light orange oil (6.88 gm, 65%).

NMR (CDCl₂): 7.48-7.28(m, 1H), 7.20-6.80(m, 2H), 4.0-3.67(q, J=7.2 Hz, 1H), 3.40-2.16(m, 4H), 1.48-1.28(d, J=7.2 Hz, 3H).

B. cis-1-Methyl-2-n-propylamino-8-bromo-1,2,3,4-tetrahydronaphthalene

To a solution of 8-bromo-1-methyl-2-tetralone (4.05 gm, 16.9 mMol) in dichloromethane (60 mL) were added magnesium sulfate (3.0 gm, 25 mMol) and n-propylamine (2.0 mL, 24.4 mMol). The mixture was stirred at room temperature for twenty hours. The reaction mixture was filtered through a bed of celite and the filtrate concentrated in vacuo to give 1-methyl-2-n-propylimino-8-bromo-1,2,3,4-tetrahydronaphthalene as a dark residue.

NMR (CDCl₃): 7.56-7.24(m, 1H), 7.20-6.80(m, 2H), 4.20-3.88(q, J=7.2 Hz, 1H), 3.56-2.0(m, 6H), 1.88-1.52(sextet, J=5.4 Hz, 2H), 1.44-1.32(d, J=7.2 Hz, 3H), 1.16-0.84(t, J=5.4 Hz, 3H).

To a solution of the preceding dark residue in tetrahydrofuran (60 mL) were added sodium cyanoborohydride (1.8 gm, 29 mMol), and the solution was saturated with hydrogen chloride. The resulting mixture was stirred for eighteen hours at room temperature. The reaction mixture was then poured into cold water (200 mL), made strongly basic (NaOH), and stirred for two hours. The reaction mixture was then made acidic (HCl) and extracted well with diethyl ether. The remaining aqueous phase was made basic (NH₄OH) and extracted well with dichloromethane. These organic phases were combined, dried (Na₂SO₄), and concentrated in vacuo to give a light yellow oil. Purification by flash chromatography (20% hexane in diethyl ether+tr. NH₄OH) gave the title compound as a colorless oil (1.47 gm, 31%).

NMR (CDCl₃): 7.4-7.19(m, 1H), 7.04-6.78(m, 2H), 3.60-3.08(m, 1H), 3.00-2.41(m, 4H), 1.90-1.35(m, 4H), 1.35-0.70(m, 8H).

(The trans-isomer of the title compound was also isolated as a colorless oil (680 mg, 14%)).

C. cis-1-Methyl-2-di-n-propylamino-8-bromo-1,2,3,4-tetrahydronaphthalene

To a solution of cis-1-Methyl-2-n-propylamino-8-bromo-1,2,3,4-tetrahydronaphthalene (1.47 gm, 5.2 mMol) in acetonitrile (30 mL) were added 1-iodopropane (.59 mL, 5.8 mMol) and proton sponge (2.2 gm, 10.4 mMol), and the mixture was stirred at 50° C. for eighteen hours. The colorless suspension was filtered and the filtrate concentrated in vacuo to give a light yellow oil. Purification by flash chromatography (20% diethyl ether in hexane+tr. NH₄OH) gave the desired compound as a colorless glass (330 mg, 20%).

NMR (CDCl₃): 7.40-7.15(dd, J=3.2 Hz, 7.2 Hz, 1H), 7.0-6.68(m, 2H), 3.50-3.12(m, 1H), 3.0-2.40(m, 6H), 2.0-1.68(m, 2H), 1.68-1.20(m, 5H), 1.20-1.04(d, J=7.2 Hz, 3H), 1.00-0.72(t, J=5.4 Hz, 6H).

D. cis-1-Methyl-2-di-n-propylamino-8-thiomethyl-1,2,3,4-tetrahydronaphthalene To a solution of cis-1-Methyl-2-n-dipropylamino-8-bromo-1,2,3,4-tetrahydronaphthalene (330 mg, 1.02 mMol) in tetrahydrofuran (10 mL) at −78° C. were added n-butyllithium in hexane (1.6 M, 1.1 mL, 1.8 mMol), and the solution was stirred at −78° C. for one hour. To the yellow solution was added dimethyl disulfide (0.11 mL, 1.22 mMol), and the solution was allowed to warm to room temperature. The now colorless solution was poured into water, made acidic (HCl), and extracted well with diethyl ether. The remaining aqueous phase was made basic (NH₄OH) and extracted well with dichloromethane. These organic extracts were combined, dried (Na₂SO₄), and concentrated in vacuo to give a colorless oil. Purification by flash chromatography (20% diethyl ether in hexane+tr. NH₄OH) gave the desired compound as a colorless, viscous oil (240 mg, 81%). The hydrobromide salt was formed. Recrystallization (acetone/hexane) gave a colorless crystalline solid (m.p.=149°-150° C.).

Analysis: Calculated for C₁₈H₂₉NS.HBr: Theory: C, 58.05; H, 8.12; N, 3.76; Found: C, 57.84; H, 8.12; N, 3.92.

MS: 293(1), 292(3), 291(10), 290(2), 266(1), 265(6), 264(20), 262(100) 192(10), 191(65), 151(25), 144(66), 115(28), 72(42).

NMR (CDCl₃): 7.16-6.66(m, 3H), 3.56-3.12(m, 1H), 3.00-2.44(m, 6H), 2.40(s, 3H), 2.00-1.68(m, 2H), 1.68-1.19(m, 5H), 1.19-1.10(d, J=7.2 Hz, 3H), 1.00-0.70(t, J=7.2 Hz, 6H).

PREPARATION EXAMPLE 9

Preparation of (R)-2-Di-n-propylamino-8-thiomethyl-1,2,3,4-tetrahydronaphthalene and (S)-2-Di-n-propylamino-8-thiomethyl-1,2,3,4-tetrahydronaphthalene.

A. N-[1-(4'-Nitrophenyl)ethyl]-N-(8-bromo-2-tetralin)-amine

A solution of 50 g of Na₂CO₃ in 300 mL of water was used to convert 66 g (0.30 mol) of the hydrochloride salt of (S)-(−)-α-methyl-4′-nitrobenzylamine to its free base. The free base was extracted into $CH_2Cl_2$. This solvent was then removed under vacuum, and the residue was dissolved in 700 mL of acetonitrile. To this solution were added successively 4.5 mL (0.08 mol) of HOAc, 4.9 g (0.08 mol) of $NaCNBH_3$, 65 g (0.29 mol) of 8-bromo-2-tetralone, and 20 g of 3A molecular sieves. The mixture was stirred under nitrogen for 16 h. Another 31.4 g (0.50 mol) of $NaCNBH_3$ was added, followed by 13.5 mL (0.24 mol) of HOAc. After 4 more hours an addition of 2 mL of HOAc was made, followed at two hour intervals by two more such additions. After stirring for another 16 h the mixture was filtered, and most of the acetonitrile was removed under vacuum. The residual mixture was poured into cold $Na_2CO_4$ solution and extracted with $CH_2Cl_2$. The extract was washed with NaCl solution and dried over $Na_2SO_4$. The $CH_2Cl_2$ was evaporated leaving the crude product as a viscous brown oil. The crude product was taken up in 300 mL of ether and then extracted into a solution of 50 g of tartaric acid in 1.5 L of 30% methanol in water. The aqueous layer was washed twice with fresh ether, then basified with sat. $Na_2CO_3$ solution and extracted into $CH_2Cl_2$. This extract was washed with NaCl solution and dried over $Na_2SO_4$. Removal of the solvent under vacuum gave 84.9 g (78% yield) of the product as an amber oil which appeared to be clean by NMR.

B.
N-[1-(4′-Nitrophenyl)ethyl]-N-(8-bromo-2-tetralin)propionamides

The compound from Part A (84.9 g, 0.23 mol) was dissolved in 1 L of $CH_2Cl_2$. This solution was treated with 71 mL (0.51 mol) of triethylamine and then slowly with 42 mL (0.48 mol) of propionyl chloride. The mixture was stirred for 16 h. It was then treated with cold $Na_2CO_3$ solution. After stirring vigorously for three hours, the $CH_2Cl_2$ layer was separated. This solution was washed with aqueous tartaric acid solution and then with $Na_2CO_3$ solution. After drying over $Na_2SO_4$, the $CH_2Cl_2$ was evaporated leaving 101 g of the crude diastereomeric mixture of amides. The diastereomers were separated by chromatographing in 20-30 g runs on an HPLC system that employed columns containing about 400 g of silica gel ("Prep 500"). The solvent system was a gradient proceeding from pure toluene to 20% EtOAc in toluene. The total weight of the first diastereomer (S,R) from the column was 49.6 g. The second diastereomer (S,S) weighed 40.6 g. Both diastereomers were viscous oils. Both contained about 2 % toluene. A satisfactory analysis was obtained for the S,S diastereomer after rigorous drying of a small sample. Slightly high carbon and low bromine percentages in the sample of the S,R diastereomer suggested that a trace of solvent had persisted even after drying. Yields of the two diastereomers were approximately 48% and 40%, respectively.

(S,R)-Diastereomer:
OR: $[\alpha]_D^{25} +9.4°$ (C=10, MeOH)
Analysis: Calculated for $C_{21}H_{23}BrN_2O_3$: Theory: C, 58.48; H, 5.38; N, 6.49; Br, 18.53; Found: C, 60.07; H, 5.61; N, 6.28; Br, 17.76.
MS: 433(1), 431(1), 361(3), 359(3), 210(100), 208(100), 129(67), 57(54).
UV (EtOH): $\lambda_{max}$ 271 nm (ε9600)
IR ($CHCl_3$): $\lambda_{max}$ 1642 cm$^{-1}$:
(S,S)-Diastereomer:
OR: $[\alpha]_D^{25} -114°$ (C=10, MeOH)
Analysis: Calculated for $C_{21}H_{23}BrN_2O_3$: Theory: C, 58.48; H, 5.38; N, 6.49; Br, 18.53; Found: C, 58.66; H, 5.43; N, 6.37; Br, 18.33.
MS: 433(1), 431(1), 361(5), 359(5), 210(100), 208(100), 129(99), 57(92).
UV (EtOH): $\lambda_{max}$ 273 nm (ε9000)
IR ($CHCl_3$): $\lambda_{max}$ 1642 cm$^{-1}$:

C.
(S,R)-N-[1-(4′-Nitrophenyl)ethyl]-N-(8-bromo-2-tetralin)-1-propylamine

A solution of 49 g (0.114 mol) of the S,R-diastereomer from Part B in 200 mL of THF was added gradually to 230 mL of ice cooled IM borane in THF. The solution was then refluxed under nitrogen for 2 h. After the solution was allowed to cool, it was carefully treated with 100 mL of MeOH. This solution was stirred for 1 h. The solvents were evaporated under vacuum, and the residue was taken up in a mixture of 250 mL of DMSO and 30 mL of water. This solution was heated on a steam bath for 1 h. It was then cooled and extracted with $CH_2Cl_2$. The extracts were washed with NaCl solution and dried over $Na_2SO_4$. The $CH_2Cl_2$ was evaporated, and the crude free base was converted to its HCl salt by dissolving in 1 L of ether and adding 50 mL of 2.6M HCl in ether. The salt was collected and washed with fresh ether. The dried salt, which weighed 50.4 g (97% yield), analyzed satisfactorily.
OR: $[\alpha]_D^{25} +28°$ (C=10, MeOH)
Analysis: Calculated for $C_{21}H_{25}BrN_2O_2 \cdot HCl$:
Theory: C, 55.58; H, 5.78; N, 6.17; Cl, 7.81; Br, 17.61; Found: C, 55.32; H, 5.94; N, 5.97; Cl, 7.61; Br, 17.33.
MS: 418(14), 416(15), 389(73), 387(71), 240(61), 238(68), 130(100), 104(59).
UV (EtOH): $\lambda_{max}$ 267 nm (ε10,000)

D.
(S,S)-N-[1-(4′-Nitrophenyl)ethyl]-N-(8-bromo-2-tetralin)propylamine

The reduction procedure described in Part C was used to reduce 40 g (0.093 mol) of the S,S diastereomer of the analogous amide. Elemental analysis indicated that the crude HCl salt, obtained in 98% yield, was slightly impure.
OR: $[\alpha]_D^{25} -94°$ (C=10, MeOH)
Analysis: Calculated for $C_{21}H_{25}BrN_2O_2 \cdot HCl$: Theory: C, 55.58; H, 5.78; N, 6.17; Found: C, 55.13; H, 5.94; N, 5.69.
MS: 418(21), 416(20), 389(79), 387(78), 240(54), 238(57), 130(100), 104(74).
UV (EtOH): $\lambda_{max}$ 269 nm (ε10,000)

E. (R)-8-Bromo-2-(N-propylamino)tetralin

A solution of 12.5 g (27.6 mmol) of the HCl salt from Part C (S,R diastereomer) in 200 mL of MeOH was hydrogenated for 8 h at 40 psi over 0.5 g of sulfided 5% platinum on carbon. After filtering off the catalyst, most of the MeOH was evaporated under vacuum without heat. Thorough ether washing of the methanolic slurry that remained afforded 6.55 g (78% yield) of the HCl salt of the title compound. A satisfactory analysis was obtained without without further purification.
OR: $[\alpha]_D^{25} +54°$ (C=8, MeOH)
Analysis: Calculated for $C_{13}H_{18}BrN \cdot HCl$: Theory: C, 51.25; H, 6.29; N, 4.60; Br, 26.23; Cl, 11.64; Found: C, 51.48; H, 6.41; N, 4.47; Br, 26.25; Cl, 11.63.

MS: 269(24), 267(23), 240(63), 238(66), 211(30), 209(34), 130(85), 56(100).

NMR (DMSOd₆): ε 0.97 (t, 3H), 1.71 (sextet, 2H), 1.79 (sextet, 1H), 2.27 (broad d, 1H), 2.75 (qt, 1H), 2.88 (broad t, 2H), 2.96 (mult, 2H), 3.25 (qt, 1H), 3.48 (broad mult, 1H), 7.12 (t, 1H), 7.18 (d, 1H), 7.49 (d, 1H), 9.19 (broad s, 2H).

F. (S)-8-Bromo-2-(N-propylamino)tetralin

Hydrogenation of the HCl salt of the S,S diastereomeric amine from Part D in a manner analogous to that described above gave a 94% yield of the HCl salt of the title compound. In this case the crude product showed minor impurities. A small sample was recrystallized from i-PrOH for analysis.

OR: $[\alpha]_D^{25} - 54°$ (C=10, MeOH)

Analysis: Calculated for $C_{13}H_{18}BrN \cdot HCl$: Theory: C, 51.25; H, 6.29; N, 4.60; Br, 26.23; Cl, 11.64; Found: C, 51.31; H, 6.30; N, 4.41; Br, 26.44; Cl, 11.81.

MS: 269(24), 267(23), 240(63), 238(66), 211(30), 209(34), 130(85), 56(100).

NMR (DMSOd₆): 0.97 (t, 3H), 1.71 (sextet, 2H), 1.79 (sextet, 1H), 2.27 (broad d, 1H), 2.75 (qt, 1H), 2.88 (broad t, 2H), 2.96 (mult, 2H), 3.25 (qt, 1H), 3.48 (broad mult, 1H), 7.12 (t, 1H), 7.18 (d, 1H), 7.49 (d, 1H), 9.19 (broad s, 2H).

G. (S)-8-Bromo-N,N-dipropyl-2-aminotetralin

To a solution of (S)-8-Bromo-N-propyl-2-aminotetralin (5.0 gm, 18.6 mMol) as produced in Part F in acetonitrile (75 mL) were added n-propyl iodide (3.0 mL, 31 mMol), followed by powdered potassium carbonate (4.0 gm, 29 mMol), and the reaction mixture was stirred for the weekend at 50° C. The reaction mixture was then cooled to room temperature and filtered. The filtrate was concentrated in vacuo to give a yellow oil. Purification by flash chromatography (2:1 hexane:diethyl ether+tr. NH₄OH) gave the title compound as a colorless oil (3.6 gm, 62 %).

NMR(CDCl₂): δ7.39(d, J=8.01 Hz, 1H), 6.98(m, 2H), 2.90(m, 4H), 2.53(m, 5H), 2.02(m, 1H), 1.50(m, 5H), .91(t, J=7.30 Hz, 6H).

H. (R)-8-Bromo-N,N-dipropyl-2-aminotetralin (R)-8-Bromo-N-propyl-2-aminotetralin (10.5 gm, 39.2 mMol) as produced in Part E was treated as described in Part G to give the title compound as a colorless oil (9.6 gm, 80%). The NMR spectrum recorded for this compound was identical to the spectrum recorded for the compound of Part G.

I. (S)-8-Thiomethyl-N,N-dipropyl-2-aminotetralin hydrochloride

To a solution of (S)-8-Bromo-N,N-dipropyl-2-aminotetralin (16.4 gm, 52.9 mMol) from Part G in tetrahydrofuran (400 mL) at −78° C. were added a solution of n-butyllithium in hexane (1.6 M, 39.7 mL, 63.5 mMol), and the solution was allowed to stir at this temperature for 1.5 hours. To the solution were then added dimethyl disulfide (9 mL, 100 mMol), and the reaction mixture was allowed to warm gradually to room temperature. The reaction mixture was then diluted with water and made acidic with 10% hydrochloric acid. The aqueous mixture was then extracted once with diethyl ether and the ether phase discarded. The remaining aqueous was made strongly basic with ammonium hydroxide and then was extracted well with dichloromethane. The organic extracts were combined, washed with saturated aqueous sodium chloride, dried over sodium sulfate, and concentrated in vacuo to give a yellow oil. Purification by flash chromatography (2:1 hexane:diethyl ether+tr. NH₄OH) gave a light yellow oil. This oil in diethyl ether was converted to the hydrochloride salt. Crystallization (ethanol/diethyl ether) gave the title compound as a colorless, crystalline solid (11.7 gm, 70%, m.p.=178.5°-180° C.).

OR: $[\alpha]_D^{25} - 65.14°$

Analysis Calculated for $C_{17}H_{27}NS \cdot HCl$: Theory: C, 65.04; H, 8.99; N, 4.46; Found: C, 65.32; H, 9.13; N, 4.48.

MS: 278(6), 277(19), 250(7), 249(20), 248(100), 179(18), 178(23), 177(67), 130(47), 129(39), 128(32).

NMR(CDCl₃) δ7.13(t, J=9 Hz, 1H), 7.00(d, J=9 Hz, 1H), 6.90(d, J=9 Hz, 1H), 2.95(m, 4H), 2.50(m, 5H), 2.48(s, 3H), 2.03(m, 1H), 1.54(m, 5H), 0.92(t, J=6 Hz, 6H).

J. (R)-8-Thiomethyl-N,N-dipropyl-2-aminotetralin hydrochloride (R)-8-Bromo-N,N-dipropyl-2-aminotetralin (17 gm, 54.8 mMol) from Part H was treated as described in Part I to give the title compound as a colorless, crystalline solid (10.5 gm, 61%, m.p.=177.5°-178.5° C.).

OR: $[\alpha]_D^{20}(H_2O) = +64.85°$

Analysis Calculated for $C_{17}H_{27}NS \cdot HCl$: Theory: C, 65.04; H, 8.99; N, 4.46; Found: C, 65.32; H, 9.02; N, 4.50.

PREPARATION EXAMPLE 10

Preparation of 3-(Di-n-propylamino)-5-methylthio-chromane hydrochloride.

A. Allyl 3-bromophenyl ether

The title compound was synthesized in 91% yield from 3-bromophenol by the procedure described in *Journal of Organic Chemistry*, 26, 3631, (1961).

B. 2-Allyl-3-bromophenol

The title compound was synthesized from allyl 3-bromophenyl ether by an ortho Claisen rearrangement in dimethylaniline as described in *Helvetica Chemica Acta*, 56(1), 14, (1973).

C. 2-Allyl-3-(carboxymethoxy)bromobenzene

To a solution of the product from Part B (15.2 gm, 71.4 mMol) in acetonitrile (350 mL) were added ethyl chloroformate (9.6 gm, 78.5 mMol) and potassium carbonate (19.7 gm, 143 mMol). The reaction mixture was stirred at 60° C. for 66 hours. After this time the reaction mixture was filtered and concentrated in vacuo to give the crude product as a light yellow oil. Purification by flash chromatography (1:1 hexane:diethyl ether) gave the desired compound as a colorless oil (16.6 gm, 78%).

NMR(CDCl₃): δ 7.22(d, J=8.05 Hz, 1H), 7.03(t, J=8.12 Hz, 1H), 6.70(d, J=8.26 Hz, 1H), 6.00(m, 1H), 5.02(m, 2H), 4.64(s, 2H), 4.27(q, J=7.22 Hz, 2H), 3.67 (d, J=6.25 Hz, 2H), 1.30(t, J=7.08 Hz, 3H).

D. 2-Formylmethyl-3-(carboxymethoxy)bromobenzene

A solution of the product from Part C (16.6 gm, 55.5 mMol) in absolute ethanol (500 mL) was cooled to −78° C., and then ozone was bubbled into the reaction mixture. After 20 minutes the solution had become light blue and all of the starting material had been consumed (TLC 1:1 hexane:diethyl ether). The reaction mixture was allowed to warm gradually to room temperature. At this point a colorless solid had precipitated, and the suspension was again cooled to −78° C. Dimethyl sulfide (7.3 mL, 100 mMol) was added dropwise, and then the reaction mixture was allowed to warm gradually to room temperature. Volatiles were removed in vacuo to give the title compound as a light yellow oil (18.3 gm, 100+%).

IR(thin film): 1022.5, 1073.1, 1189.7, 1203.7, 1725.4, 1754.7cm$^{-1}$.

MS(FD): 302(100), 300(90).

NMR(CDCl$_3$): δ 9 70(s, 1H), 7.25(d, J=8.06 Hz, 1H), 7.11(t, J=8.16 Hz, 1H), 6.74(d, J=8.13 Hz, 1H), 4.62(s, 2H), 4.22(q, J=7.14 Hz, 2H), 4.00(s, 2H), 1.26(t, J=6.81 Hz, 3H).

E. 2-Carboxymethyl-3-(ethoxycarbonylmethoxy)bromobenzene

To approximately 55 mMol of crude product from Part D in acetone (300 mL) were added Jones'Reagent until a bright orange color persists in solution. A dark green solid formed as the temperature gradually increased to reflux. Isopropanol was added to destroy any excess chromium trioxide, and then the reaction mixture was diluted with water and then extracted well with diethyl ether. The ether phases were combined and then washed well with water. The remaining ether phase was extracted three times with saturated aqueous sodium bicarbonate (100 mL). These extracts were then made strongly acidic with hydrochloric acid (10%) and extracted well with chloroform:isopropanol (3:1). The combined organic extracts were then washed with saturated aqueous sodium chloride, dried over sodium sulfate and concentrated in vacuo to give the title compound as a yellow viscous oil (12.3 gm, 71%).

IR(thin film): 1191.1, 1205.8, 1278.8, 1449.3, 1465.3, 1574.6, 1171.1, 1739.3, 1754.8 cm$^{-1}$.

MS(FD): 318(100), 316(90).

NMR(CDCl$_3$): δ 7.26(d, J=8.14 Hz, 1H), 7.12(t, J=8.17 Hz, 1H), 6.75(d, J=8.12 Hz, 1H), 4.66(s, 2H), 4.25(q, J=6.84 Hz, 2H), 4.04(s, 2H), 1.29(t, J=7.22 Hz, 3H).

F. 2-Carboxymethyl-3-(carboxymethoxy)bromobenzene, diethyl ester

A solution of the product from Part E (12.3 gm, 38.8 mMol) in absolute ethanol (400 mL) was saturated with hydrogen chloride, and the solution was allowed to stir for 18 hours at room temperature. Volatiles were removed in vacuo to give a light brown oil. Purification by flash chromatography (1:1 hexane:diethyl ether) gave the desired compound as a colorless oil (12.4 gm, 93%).

NMR(CDCl$_3$): δ 7.24(d, J=8.09 Hz, 1H), 7.10(t, J=8.53 Hz, 1H), 6.73(d, J=8.13 Hz, 1H), 4.63(s, 2H), 4.21(m, 4H), 3.97(s, 2H), 1.27(m, 6H).

G. Mixture of 4-Ethoxycarbonyl-5-bromo-3-chromanone and 2-ethoxycarbonyl-5-bromo-3-chromanone A solution of the diester from Part F (6 gm, 17.4 mMol) in tetrahydrofuran (50 ml) was added dropwise to a solution of potassium t-butoxide (3.90 gm, 34.8 mMol) in tetrahydrofuran (200 mL). The reaction mixture was then immediately poured over ice and the solution made acidic with 10% hydrochloric acid. The mixture was then extracted well with diethyl ether. The organic phases were combined, washed with saturated aqueous sodium chloride, dried over sodium sulfate, and concentrated in vacuo to give a yellow solid. Purification by flash chromatography (1:1 hexane:diethyl ether) gave two compounds. 2-Ethoxycarbonyl-5-bromo-3-chromanone was recovered as colorless crystals (1.3 gm).

NMR(CDCl$_3$): δ 7.25(d, J=8.10Hz, 1H), 7.05(m, 2H), 4.42(q, J=6.84 Hz, 2H), 3.70(s, 2H), 1.58(br s, 1H), 1.42(t, J=7.10 Hz, 3H).

The 4-ethoxycarbonyl-5-bromo-3-chromanone was recovered as a light yellow viscous oil (1.7 gm).

NMR(CDCl$_3$): δ 7.26(d, J=8.14 Hz, 1H), 7.18(t, J=8.18 Hz, 1H), 7.04(d, J=8.12 Hz, 1H), 4.90(s, 1H), 4.75(d, J=16 Hz, 1H), 4.22(m, 3H), 1.27(t, J=7.05 Hz, 3H).

H. 5-Bromo-3-chromanone

A suspension of 2-ethoxycarbonyl-5-bromo-3-chromanone (300 mg, 1 mMol) in methanol (5 mL) and 10% hydrochloric acid (3 mL) was heated at reflux for 2 hours. All of the solid had not dissolved; therefore, trifluoroacetic acid (1 mL) was added, and heating was continued for 18 hours. The reaction mixture was diluted with water and extracted well with diethyl ether. The ether phases were combined, dried over sodium sulfate, and concentrated in vacuo to give a yellow glass. Purification by flash chromatography (1:1 hexane:ether) gave the title compound as a light yellow glass (120 mg, 53%).

NMR(CDCl$_3$): δ 7.32(d, J=8.08 Hz, 1H), 7.12(t, 8.19 Hz, 1H), 7.02(d, J=8.05 Hz, 1H), 4.41(s, 2H), 3.69(s, 1H).

I. 5-Bromo-3-di-n-propyl-3-aminochromane

To a solution of the product from Part H (620 mg, 2.73 mMol) in toluene (20 mL) were added dipropylamine (0.7 mL, 6 mMol) and p-toluenesulfonic acid (100 mg, 0.52 mMol), and the mixture was heated at reflux with constant water removal (Dean-Stark trap). After 3 hours the reaction mixture was cooled to room temperature and the volatiles removed in vacuo to give a dark reddish-orange residue. This material was dissolved in tetrahydrofuran (40 mL), sodium cyanoborohydride (400 mg, 6.4 mMol) was added and the solution was saturated with hydrogen chloride. The reaction mixture was stirred for 18 hours at room temperature. The reaction mixture was then poured into 15% sodium hydroxide (100 mL) and was stirred vigorously for 2 hours. The reaction mixture was then extracted well with diethyl ether. The organic phases were combined, dried over sodium sulfate, and concentrated in vacuo. The residue was suspended in 10% hydrochloric acid and the aqueous extracted once with diethyl ether. This ether extract was discarded and the remaining aqueous made basic with concentrated ammonium hydroxide and then extracted well with dichloromethane. The combined organics were washed with saturated aqueous sodium chloride, dried over sodium sulfate, and concentrated in vacuo to give a light yellow oil. Purification by flash chromatography (4:1 hexane:diethyl ether+tr. NH$_4$OH) gave the title compound as a colorless oil (420 mg, 50%).

NMR(CDCl$_3$): δ 7.16(d, J=7.77 Hz, 1H), 6.98(t, J=7.85 Hz, 1H), 6.80(d, J=8.16 Hz, 1H), 4.28(m, 1H), 3.78(t, J=8.30 Hz, 1H), 3.17(m, 1H), 2.93(m, 1H), 2.67(m, 1H), 2.53(t, J=7.42 Hz, 4H), 1.49(sextet, J=7.32 Hz, 4H), 0.91(t, J=7.28 Hz, 6H).

J. 3-Di-n-propyl-amino-5-thiomethyl-chromane hydrochloride

To a solution of the product from Part I (420 mg, 1.35 mMol) in tetrahydrofuran (25 mL) at −78° C. was added a solution of n-butyllithium in hexane (1.6 M, 2 mL, 3.2 mMol), and the resulting solution was stirred at −78° C. for 1 hour. To the mixture was then added dimethyl disulfide (.25 mL, 2.5 mMol), and the reaction mixture allowed to warm gradually to room temperature. The reaction mixture was diluted with water and made acidic with hydrochloric acid. The aqueous was then extracted well with diethyl ether, and the ether etracts were discarded. The remaining aqueous was made basic with concentrated ammonium hydroxide and extracted well with dichloromethane. The organics were dried over sodium sulfate and concentrated in vacuo to give a colorless oil. Purification by flash chromatography (1:1 hexane:diethyl ether+tr. NH4OH) gave a colorless, viscous oil (290 mg, 77%). The hydrochloride salt was formed. Recrystallization (ethanol/diethyl ether) gave the title compound as colorless crystals (m.p.=181°-183° C.).

Analysis: Calculated for C16H25NOS.HCl: Theory: C, 60.83; H, 8.30; N, 4.43; Found: C, 61.09; H, 8.32; N, 4.44.

MS: 280(6), 279(28), 252(8), 251(23), 250(100), 179(74), 98(50).

NMR(CDCl3): δ 7.10(t, J=8.01 Hz, 1H), 6.75(d, J=7.89 Hz, 1H), 6.63(d, J=7.97 Hz, 1H), 4.30(m, 1H), 3.78(t, J=8.30 Hz, 1H), 3.20(m, 1H), 2.89(m, 1H), 2.56(m, 5H), 2.45(s, 3H), 1.48(sextet, J=7.32 Hz, 4H), .91(t, J=7.31 Hz, 6H).

4-amino-1,3,4,5-tetrahydrobenz[c,d]indoles

A second class of direct acting 5HT1A agonists comprises the 4-amino-1,3,4,5-tetrahydrobenz[c,d]indoles. Representative examples of compounds within this class include those disclosed in EPA 153083, published Aug. 28, 1985, which describes 4-amino-6-substituted-1,3,4,5-tetrahydrobenz[c,d]indoles having the Formula

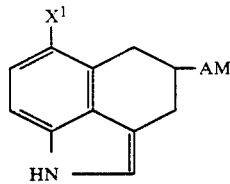

II wherein AM is NR4R5 wherein R4 and R5 are individually hydrogen, methyl, ethyl, n-propyl or allyl, and X1 is OC1-3alkyl, O-acyl, OH, a halogen, CN, CONH2 NH2 or NO2; and pharmaceutically acceptable salts thereof.

Compounds according to this Formula have an asymmetric center at C-4. As such, each of the compounds exists as its individual d- and l-stereoisomers as well as the racemic mixture of such isomers. Accordingly, the compounds of the present invention include not only the dl-racemates but also their respective optically active d- and l-isomers.

EPA Publication No. 153,083 which is incorporated by reference herein in its entirety also describes methods for preparing these compounds.

U.S. Pat. No. 4,745,126, which is incorporated by reference herein in its entirety describes additional examples of and methods for preparing compounds within the scope of the above Formula II, including stereoisomers and pharmaceutically acceptable salts.

Further examples of 1,3,4,5-tetrahydrobenz-[c,d]indoles including pharmaceutically acceptable salts and stereoisomers are those disclosed in EPA 0148440 published July 17, 1985 which is incorporated by reference herein in its entirety. The compounds disclosed in EPA 0148440 have the above Formula II where X is C1-C4 alkoxy, OH, SH or C1-C4 alkylthio, and R4 and R5 are hydrogen, C1-C4 alkenyl, or, together with the N atom, form a 5-or 6-membered heterocyclic ring which can optionally be substituted by 1 or 2 C1-C6 alkyl groups. Methods for preparing the compounds, including 6-mercapto and 6-alkylthio derivatives, are described.

Still further examples of 1,3,4,5-tetrahydrobenz[c,d]indoles within this second class are those having the Formula

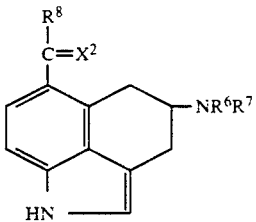

IIA wherein:

R6 is hydrogen, C1-C4 alkyl, allyl or

R7 is hydrogen, C1-C4 alkyl or allyl;
R8 is hydrogen, C1-C3 alkoxy or C1-C3 alkylthio;
R9 is hydrogen, methyl, ethyl or vinyl;
X2 is O or S; or a pharmaceutically acceptable salt thereof.

In the above Formula IIA, C1-C4 alkyl represents a straight or branched alkyl chain having from one to four carbon atoms. Typical C1-C4 alkyl groups include methyl, ethyl, n-propyl, isopropyl, n-butyl, sec-butyl and the like.

C1-C3 Alkoxy represents methoxy, ethoxy, n-propoxy and isopropoxy.

C1-C3 Alkylthio represents methylthio, ethylthio, n-propylthio and isopropylthio.

Preferably X2 is oxygen, R6 and R7 are both C1-C4 alkyl, and especially n-propyl, and R8 is C1-C3 alkoxy, and especially methoxy or ethoxy.

As pointed out above, the Formula IIA compounds includes the pharmaceutically-acceptable salts of those compounds. Since these compounds are amines, they are basic in nature and accordingly react with any number of inorganic and organic acids to form pharmaceutically acceptable salts such as hydrochloric acid, nitric acid, phosphoric acid, sulfuric acid, hydrobromic acid, hydroiodic acid, phosphorous acid and others, as well as salts derived from non-toxic organic acids such as aliphatic mono and dicarboxylic acids, phenyl-substituted alkanoic acids, hydroxyalkanoic and hydroxyalkandioic acid, aromatic acids, aliphatic and aromatic sulfonic acids. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, tartrate isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, naphthalene-1-sulfonate, naphthalene-2-sulfonate and mesylate.

The compounds of Formula IIA have an asymmetric center at the carbon atom at the 4-position of the tetrahydrobenz[c,d]indole ring. As such the compounds can exist as either the racemic mixture, or as the individual stereoisomers. All such types of compounds are contemplated by the leave as is.

The following list illustrates representative compounds of Formula IIA.

(±)-4-(dimethylamino)-1,3,4,5-tetrahydrobenz[c,-d]indole-6-carbothioic acid, S-methyl ester (±)-4-(di-n-propylamino)-1,3,4,5-tetrahydrobenz[c,-d]indole-6-carbothioic acid, O-ethyl ester (+)-4-(methylethylamino)-1,3,4,5-tetrahydrobenz[c,-d]indole-6-carbodithioic acid, methyl ester (+)-4-(n-butylamino)-1,3,4,5-tetrahydrobenz-c,d]indole-6-carboxylic acid, ethyl ester (−)-4-(n-propylamino)-1,3,4,5-tetrahydrobenz-c,d]indole-6-carbothioic acid, S-methyl ester (±)-4-amino-1,3,4,5-tetrahydrobenz[c,d]indole-carbodithioic acid, n-propyl ester (+)-4-(allylamino)-1,3,4,5-tetrahydrobenz-c,d]indole-6-carbodithioic acid, ethyl ester (±)-4-(di-n-propylamino)-1,3,4,5-tetrahydro-benz[c,-d]indole-6-carbothioic acid, S-methyl ester (−)-4-(methylamino)-1,3,4,5-tetrahydrobenz-c,d]indole-6-carboxylic acid, n-propyl ester (+)-4-amino-1,3,4,5-tetrahydrobenz[c,d]indole-6-carboxylic acid, methyl ester (±)-4-(diethylamino)-1,3,4,5-tetrahydrobenz-c,d]indole-6-carboxylic acid, n-propyl ester maleate (±)-4-(dimethylamino)-1,3,4,5-tetrahydrobenz-c,d]indole-6-carboxylic acid, methyl ester (−)-4-(methylisopropylamino)-1,3,4,5-tetrahydrobenz[c,d]indole-6-carbothioic acid, O-methyl ester (+)-4-(di-n-propylamino)-1,3,4,5-tetrahydrobenz[c,-d]indole-6-carboxaldehyde (±)-4-(ethylamino)-1,3,4,5-tetrahydrobenz-c,d]indole-6-carbothioic acid, S-methyl ester (±)-4-(methylethylamino)-1,3,4,5-tetrahydrobenz[c,-d]indole-6-carboxylic acid, ethyl ester (+)-4-(sec.-butylamino)-1,3,4,5-tetrahydroindole-6-carbodithioic acid, methyl ester Among the 5-HT1A agonist compounds included in this class as described above, including these compounds described in references that have been incorporated by reference, certain of these compounds are preferred. The preferred compounds are those of Formula II where $R^4$ and $R^5$ are individually selected from hydrogen, methyl, ethyl, n-propyl and allyl;

$X^1$ is OH, $C_1$-$C_3$ alkoxy, $C_1$-$C_3$ alkylthio, O-acyl, halogen, CN, $CONH_2$, $NH_2$, $NO_2$, $COO(C_1$-$C_3$ alkyl), CHO, or C(O)S ($C_1$-$C_3$) alkyl; or a pharmaceutically acceptable acid addition salt thereof.

The compounds of Formula IIA are preferably prepared by the following process. A 4-amino-6-bromotetrahydrobenz[c,d]indole is converted to a 1-potassium-6-lithium substituted derivative which is treated with an appropriate electrophile. The compound thus prepared may require deblocking to provide a compound of Formula IIA. This reaction may be represented by the following scheme:

wherein $R^6$, $R^7$, Rhu 8 and $X^2$ are as defined above.

According to this process, a 4-amino-6-bromotetrahydrobenz[c,d]indole 1 is combined with an equimolar to slight excess amount of potassium hydride in diethyl ether. The reagents are generally combined at a cold temperature, typically in the range of about −20° C. to about 10° C., preferably at about 0° C. The resulting mixture is next cooled to a temperature in the range of about −100° C. to about −60° C., preferably at about −78° C., and combined with a lithiating reagent, preferably in at least a two molar excess amount. Suitable lithiating reagents are selected from the group consisting of sec-butyllithium and t-butyllithium, which is preferred. The reaction is substantially complete after about 10 minutes to about 6 hours when conducted at a temperature in the range of about −100° C. to about −20° C., preferably at about −60° C. to about −40° C.

The 4-amino-6-lithiumtetrahydrobenz[c,d]indole 2 thus prepared is next converted to the 1,6-disubstituted-4-aminotetrahydrobenz[c,d]indole 3 upon reaction with an appropriate electrophile such as $R^8C(=X)Y$ wherein X is defined above and Y is a good leaving group such as cyano. Typically, a solution of the compound 2 at a temperature in the range of about $-100°$ C. to about $-60°$ C., preferably at about $-80°$ C., is added to a solution of this reagent in a mutual solvent. Typically at least a four molar excess amount of the electrophile is employed in the reaction. The reaction is substantially complete after about 10 minutes to about 2 hours when conducted at a temperature in the range of about $-40°$ C. to about $10°$ C. The desired compound is purified by quenching the reaction mixture with ice water. The mixture is washed with a water immiscible organic solvent. The organic phase is extracted with acid, and the aqueous phases are combined, made basic and the desired compound extracted with a water immiscible organic solvent. The organic solvent is then concentrated, typically under vacuum, and the desired compound 3 is further purified, if necessary, by standard procedures.

If any nitrogen atoms are acylated in the foregoing reactions the compounds of Formula IIA are prepared according to standard deblocking conditions. Deblocking generally occurs in base, such as ammonium hydroxide or an inorganic base, for example potassium carbonate, in a protic solvent such as alcohol or water. The desired compound is isolated by standard conditions and purified by crystallization from common solvents or column chromatography over solid supports such as silica gel or alumina.

Thiocarboxylic acid esters defined by Formula IIA wherein $X^2$ is sulfur form another important group of compounds that are a further embodiment of this class of compounds. The thiocarboxylic acid esters of the invention may be prepared by thiating the corresponding carboxylic acid ester or thioester. Any of several thiating agents can be employed in this reaction including phosphorous pentasulfide. Another preferred thiating agent is Lawesson's Reagent, which is 2,4-bis(4-methoxyphenyl)-1,3-dithia-2,4-diphosphetane-2,4-disulfide. This thiating agent and its general uses are described in detail in *Tetrahedron Letters*, 21, 4061 (1980). The thiation reaction is preferably carried out by combining approximately equimolar quantities of the carboxylic acid ester and thiating agent in a mutual organic solvent such as toluene or dioxane. The reaction is generally complete within about 1 hour to about 10 hours when carried out at a temperature of about $50°$ C. to about $150°$ C. The thiocarboxylic acid esters thus formed can be isolated and purified by normal methods such as crystallization and the like.

The thiocarboxylic acid esters of Formula IIA may also be prepared by reacting the 4-amino-6-lithiumtetrahydrobenz[c,d]indole 2, prepared as described above, with a thiocarbonyl reagent such as carbon disulfide or thiocarbonyl-1,1'-diimidazole, which can then be converted to a compound of Formula IIA by reaction with the desired electrophile as described above.

The compounds of Formula IIA wherein the 6-position has a carboxylic acid group may be used as intermediates to certain other compounds of Formula IIA. For example, the 6-carboxylic or 6-thiocarboxylic acids may be reacted with a reagent $R^8$ H (wherein $R^8$ is other than hydrogen) and a coupling reagent, for example any of the type of coupling reagents commonly employed in the synthesis of peptides, and the desired ester or thioester isolated. Examples of such coupling reagents include carbodiimides, such as N,N'-dicyclohexylcarbodiimide, N,N'-diisopropylcarbodiimide or N,N'-diethylcarbodiimide; the imidazoles such as carbonyl diimidazole as well as reagents such as N-ethoxycarbonyl-2-ethoxy-1,2-dihydroquinoline (EEDQ).

The compounds of Formula IIA wherein $R^8$ is hydrogen are carboxaldehydes and may be prepared by reducing a 4-amino-6-cyanotetrahydrobenz[c,d]indole with a hydride reducing agent such as diisobutylaluminum hydride, and isolating the desired compound of Formula IIA according to standard procedures.

The pharmaceutically acceptable salts of the invention are typically formed by reacting an amine of Formula IIA with an equimolar or excess amount of acid. The reactants are generally combined in a mutual solvent such as diethyl ether or benzene, and the salt normally precipitates out of solution within about one hour to about 10 days, and can be isolated by filtration.

The 4-amino-6-bromo tetrahydrobenz[c,d]indole and 6-cyano and 6-carboxylic acid starting materials used to prepare the compounds of the invention are known compounds readily prepared by prior art processes. The compounds are taught in detail by Flaugh in U.S. Pat. No. 4,576,959, incorporated by reference herein in its entirety.

The following Examples further illustrate the compounds of Formula IIA and methods for their synthesis.

PREPARATION EXAMPLE 11

($\pm$)-4-(Di-n-propylamino)-1,3,4,5-tetrahydrobenz[c,d]indole-6-carboxylic acid, methyl ester

A.

($\pm$)-1-Methoxycarbonyl-4-(di-n-propylamino)-1,3,4,5-tetrahydrobenz[c,d]indole-6-carboxylic acid, methyl ester A solution of 0.335 g (1 mmol) of 4-(di-n-propylamino)-6-bromo-1,3,4,5-tetrahydrobenz[c,d]indole in 5 ml of diethyl ether was added to a suspension of 0.19 g (1.2 mmol) of potassium hydride in a 25% by weight mineral oil dispersion in 25 ml of diethyl ether at about $0°$ C. The reaction mixture was stirred at $0°$ C. for 1 hour and cooled to approximately $-78°$ C. with an external dry ice/acetone bath. A solution of 1.7 M t-butyllithium (1.5 ml, 2.55 mmol) cooled to about $-78°$ C. was added to the reaction mixture via a cannula. The resulting mixture was allowed to warm to approximately $-40°$ C. and was stirred at that temperature for 2 hours. The turbid mixture was cooled to $-78°$ C. and a solution of 0.34 g (4 mmol) of methyl cyanoformate in 1 ml of diethyl ether was rapidly added. The mixture was allowed to warm to about $0°$ C. and was quenched with ice water. The mixture was extracted with diethyl ether. The ether extract was extracted with 1M phosphoric acid. The aqueous solution was treated with an excess amount of a saturated aqueous sodium bicarbonate solution and extracted with methylene chloride. The organic extract was dried over anhydrous sodium sulfate and concentrated under vacuum. The resulting residue was chromatographed over 5 g of silica gel while eluting first with ethyl acetate:toluene (1:9, v:v) followed by ethyl acetate:toluene (1:1, v:v). Fractions containing the major component were combined and the solvent was evaporated therefrom to provide 261 mg of ($\pm$)-1-methoxycarbonyl-4-(di-n-propylamino)-

1,3,4,5-tetrahydrobenz[c,d]indole-6-carboxylic acid, methyl ester.

B. A solution of 261 mg (0.64 mmol) of (±)-1-methoxycarbonyl-4-(di-n-propylamino)-1,3,4,-5-tetrahydrobenz[c,d]indole-6-carboxylic acid, methyl ester in 10 ml of methanol was added to a solution of 2.0 g of potassium carbonate in 10 ml of water and 20 ml of methanol. The resulting mixture was stirred at room temperature for approximately 1 hour and a thin layer chromatograph indicated that only a trace of starting material remained. The reaction mixture was diluted with an aqueous saturated sodium chloride solution and extracted several times with methylene chloride. The organic extracts were combined and washed with an aqueous sodium chloride solution and dried over anhydrous sodium sulfate. The organic phase was concentrated under vacuum to dryness to provide a crystalline residue which was recrystallized from toluene/hexane to provide 154 mg of (±)-4-(di-n-propylamino)-1,3,4,5-tetrahydrobenz[c,d]-indole-6-carboxylic acid, methyl ester. mp=132°-132.5° C.

Analysis calculated for $C_{19}H_{26}N_2O_2$ Theory: C, 72.58; H, 8.34; N, 8.91; Found: C, 72.83; H, 8.39; N, 8.88.

NMR (300 MHz, CDCl$_3$): δ 0.91 (triplet, 6H); 1.49 (sextet, 4H); 2.58 (sextet, 4H); 2.78 (triplet, 1H); 3.00 (quartet, 1H); 3.03 (triplet, 1H); 3.23 (multiplet, 1H); 3.81 (quartet, 1H); 3.91 (singlet, 3H); 6.88 (singlet, 1H); 7.14 (doublet, 1H); 7.84 (doublet, 1H); 8.02 (singlet, 1H).

PREPARATION EXAMPLE 12

(±)-4-(Di-n-propylamino)-1,3,4,5-tetrahydrobenz-[c,d]indole-6-carboxylic acid, ethyl ester A. (±)-1-Ethoxycarbonyl-4-(di-n-propylamino)-1,3,4,5-tetrahydrobenz[c,d]indole-6-carboxylic acid, ethyl ester A solution of 0.335 g (1 mmol) of 4-(di-n-propylamino)-6-bromo-1,3,4,5-tetrahydrobenz[c,d]indole in 5 ml of diethyl ether was added to a suspension of 0.19 g (1.2 mmol) of potassium hydride in a 25% by weight mineral oil dispersion in 25 ml of diethyl ether at about 0° C. The reaction mixture was stirred at 0° C. for 1 hour and cooled to about −78° C. with an external dry ice/acetone bath. A solution of 1.7M t-butyllithium (1.5 ml, 2.55 ml) cooled to −78° C. was added to the reaction mixture via a cannula. The resulting mixture was allowed to warm to about −40° C. and held there for 2 hours. The resulting turbid mixture was cooled to about −78° C. To this mixture was added a solution of 0.4 g (4 mmol) of ethyl cyanoformate in 1 ml NMR (300 MHz, CDCl$_3$): δ 0.91 (triplet, 6H); 1.42 (triplet, 3H); 1.49 (sextet, 4H); 2.58 (triplet, 4H); 2.78 (triplet, 1H); 3.00 (quartet, 1H); 3.03 (triplet, 1H); 3.23 (multiplet, 1H,); 3.83 (quartet, 1H); 4.36 (multiplet, 2H); 6.88 (singlet, 1H); 7.14 (doublet, 1H); 7.84 (doublet, 1H); 8.04 (singlet, 1H).

PREPARATION EXAMPLE 13

(±)-4-(Dimethylamino)-1,3,4,5-tetrahydrobenz[c,d]indole6-carboxaldehyde

To a suspension of 0.9 g (3.96 mmol) of (±)-4-(dimethylamino)-6-cyano-1,3,4,5-tetrahydrobenz[c,d]-indole in 10 ml of benzene stirred at room temperature under a nitrogen atmosphere was added 8.1 ml (8.1 mmol) of IM diisobutylaluminum hydride in toluene dropwise. The reaction mixture was stirred at about 50° C. for 6 hours. The mixture was cooled to room temperature and a solution of 1.0 ml of methanol in 4.5 ml of toluene was added to dissolve the precipitate that had formed. Next, 1.0 ml of water in 4.5 ml of methanol was added, and the resulting mixture was added to ice cold 0.5M hydrochloric acid and shaken. The aqueous layer and a 0.5M hydrochloric acid extraction of the separated organic phase were combined and made basic with 2M sodium hydroxide. The aqueous phase was extracted with methylene chloride, and the organic phase was washed with a saturated sodium chloride solution, dried over anhydrous sodium sulfate and concentrated under vacuum to provide an oil. The oil was chromatographed employing ethyl acetate:methanol (19:1, v:v) as the eluant. Fractions containing the major component were combined and the solvent was evaporated therefrom to provide 0.5 g of the title compound following recrystallization from ethyl acetate/toluene. mp=163° C.

Analysis calculated for $C_{14}H_{16}N_2O$ Theory: C, 73.66; H, 7.06; N, 12.27; Found: C, 73.50; H, 7.02; N, 12.17.

NMR (300 MHz, CDCl$_3$): δ 2.48 (singlet, 6H); 2.86 (quartet, 1H); 3.08 (multiplet, 2H); 3.19 (multiplet, 1H); 3.86 (broad doublet, 1H); 6.95 (singlet, 1H); 7.25 (doublet, 1H); 7.66 (doublet, 1H); 8.31 (singlet, 1H); 10.28 (singlet, 1H).

PREPARATION EXAMPLE 14

(±)-4-(Di-n-propylamino)-1,3,4,5-tetrahydrobenz[c,d]-indole-6-carboxaldehyde

A 100 ml three neck round bottom flask under a nitrogen atmosphere was charged with 0.176 g (1.1 mmol) of 25% potassium hydride in mineral oil which had been washed with heptane. To the flask was added 40 ml of diethyl ether and the mixture was cooled to about 0° C. To the mixture was added a solution of 0.335 g (1.0 mmol) of (±)-4-(di-n-propylamino)-6-bromo-1,3,4,5-tetrahydrobenz[c,d]indole in 10 ml of diethyl ether over a period of about 5 minutes. The mixture was stirred at about 0° C. for one hour, and for three hours at room temperature. The mixture was cooled to about −78° C. with an external dry ice/acetone bath and 1.47 ml of 1.7M t-butyllithium was added dropwise over a period of about 10 minutes. The mixture was warmed 5° to about −50° C. over about two hours. The mixture was again cooled to about −78° C. and 0.193 ml of dry DMF in 10 ml of diethyl ether was added. The mixture was stirred at −78° C. for 30 minutes, warmed to room temperature, and stirred overnight. To the mixture was added 50 ml of water and 25 ml of diethyl ether. The mixture was washed twice with 50 ml portions of water. The organic phase was dried over anhydrous sodium sulfate, filtered and concentrated under vacuum to provide 0.17 g of a brown oil. The oil was chromatographed over silica gel employing ethyl acetate: toluene:triethylamine (42:42:16, v:v:v) as the eluant. Fractions containing the major component were combined and the solvent was evaporated therefrom to provide 0.19 g of (±)-4-(di-n-propylamino)-1,3,4,5-tetrahydrobenz[c,d]indole-6-carboxaldehyde as a yellow oil.

NMR (300 MHz, CDCl$_3$): δ 0.95 (triplet, 6H); 1.50 (multiplet, 4H); 2.60 (triplet, 4H); 3.10 (multiplet, 4H); 3.80 (doublet, 1H); 7.00( multiplet, 3H); 8.3 (singlet, 1H); 10.3 (singlet, 1H).

Nonendogenous Indoles

A third class of direct acting 5-HT1A agonists comprises nonendogenous indole derivatives or a pharmaceutically acceptable acid addition salt thereof. These indole derivatives include various 3-substituted indoles, 5-substituted indoles and 3-substituted-5-substituted indoles. Examples of such indoles are described in Middlemiss, *Annual Reports of Medicinal Chemistry*, 21, 41-50 (Academic Press, 1986). Further examples of these indoles are described in Fuller, *Monographs in Neural Sciences*, 10, 158-181 (Karger, Basel, Switzerland 1984).

Illustrative examples of such compounds includes:
5-methoxytryptamine;
5-aminocarbonoyltryptamine;
5-methoxy-3-(1,2,3,6-tetrahydropyridine-4-yl)-indole;
N,N-di-n-propyl-5-carbamoyltryptamine;
N,N-dimethyl-5-methoxytryptamine;
N,N-diethyl-5-methoxytryptamine;
N,N-di-n-propyl-5-methoxytryptamine;
5-methoxy-3-[2-[1-(4-phenyl)-1,2,3,6-tetrahydropyridyl]ethyl]indole;
N,N-dimethyl-5-hydroxytryptamine;
N,N-dimethyltryptamine; and These compounds are prepared according to Glennon et. al., *J. Med. Chem.*, 31, 867-870 (1988) or Taylor et. al., *Molecular Pharmacology*, 34, 42 (1988) which are both incorporated by reference herein in their entirety.

At least 5-methoxytryptamine; N,N-dimethyl-5-methoxytryptamine; N,N-dimethyl-5-hydroxytryptamine; and N,N-dimethyltryptamine are commercially available from sources such as Aldrich Chemical Company, Inc., 940 West Saint Paul Avenue, Milwaukee, Wis. 53233 U.S.A., Sigma Chemical Company, P.O. Box 14508, St. Louis, Mo. 63178 U.S.A.; or both. References to the preparation of N,N-dimethlytryptamine and 5-methoxytryptamine are provided in *The Merck Index*, 10th ed., Merck & Co., Inc. (1983).

As mentioned above, useful compounds for practicing the method of the present invention includes pharmaceutically acceptable acid addition compounds. Since these compounds are amines, they are basic in nature and accordingly react with any of a number of inorganic and organic acids to form pharmaceutically acceptable acid addition salts. Acids commonly employed to form such salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid.

In addition, some of these salts may form solvates with water or organic solvents such as ethanol. Such solvates also are included within the scope of this invention.

Among the 5-HT1A agonist compounds included in this class as described above, including those compounds described in references that have been incorporated by reference, certain of these compounds are preferred. The preferred compounds are 5-methoxy-3-(1,2,3,6,-tetrahydropyridine-4-yl) indole; N,N-dipropyl-5-methoxytryptamine; and N,N-dipropyl-5-carboxamidotryptamine.

The compounds employed as initial starting materials in the synthesis of the indole compounds of this class are well known and readily synthesized by standard procedures commonly employed by those of ordinary skill in the art.

The pharmaceutically acceptable salt addition salts are typically formed by reacting a 3-substituted, 5-substituted or 3-substituted-5-substituted indole with an equimolar or excess amount of acid. The reactants are generally combined in a mutual solvent such as diethyl ether or benzene, and the salt normally precipitates out of solution within about one hour to 10 days, and can be isolated by filtration.

Aryloxypropanolamines

A fourth class of compounds acting at the 5-HT1A receptor comprises a series of aryloxypropanolamines. These compounds have the Formula

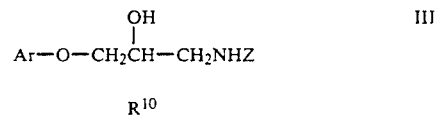

where Ar is an optionally mono- or disubstituted phenyl or naphthalene ring where the substituents are selected from allyl, $C_1$-$C_4$ alkyl, $O(C_1$-$C_4$ alkyl), —($C_1$-$C_3$ alkylidene)—O—($C_1$-$C_4$ alkyl), O-allyl, CN, NHCO($C_1$-$C_3$ alkyl), —CH$_2$CONH$_2$, trifluoromethyl, hydroxy, halo, ($C_1$-$C_4$ alkyl)-S(O)$_p$—, where p is 0, 1, or 2 and a $C_3$-$C_8$ cycloalkyl or a bicycloalkyl group of the Formula;

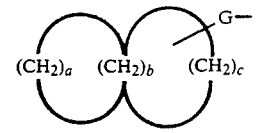

where a and c are independently 1-5, b is 0-5, and (a+c) is greater than 2; and G' is a bond or $C_1$-$C_4$ alkylidene; or where Ar is the group.

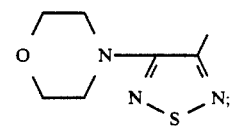

Z is a straight or branched $C_3$-$C_{10}$ alkyl; $C_4$-$C_{10}$ alkenyl; $C_4$-$C_{10}$ alkynyl group; a phenyl($C_2$-$C_{10}$) alkyl where the phenyl moiety may be substituted with a halo, $C_1$-$C_4$ alkyl, trifluoromethyl, hydroxy, $C_1$-$C_4$ alkoxy, $C_1$-$C_4$ alkyl-S(O)$_p$— where p is 0, 1, or 2; a group G-V where G is independently a bond or $C_1$-$C_4$ alkyl or phenyl, and V is $C_4$-$C_8$ cycloalkyl optionally substituted with a $C_1$-$C_4$ alkyl or phenyl; a —($C_1$-$C_4$ alkylidene)-T-($C_1$-$C_4$ alkyl) where T is —O—, —S—, —SO—, or —SO$_2$—; or a bicycloalkyl group having the Formula

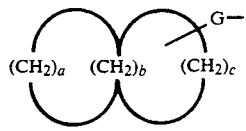

where G is as defined above and a and c are independently 1-5, b is 0-5, and (a+c) is greater than 2; $R^{10}$ is an optional methyl group substituted on one of the three connecting carbon atoms; or a pharmaceutically acceptable salt thereof.

Preferred aryloxypropanolamines have the Formula

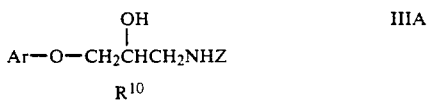

IIIA where Ar is

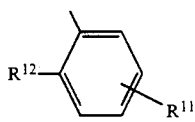

$R^{10}$ is an optional methyl group substituted on one of the three connecting carbon atoms;

$R^{11}$ is hydrogen, $C_1$-$C_4$ alkyl, trifluoromethyl, hydroxy, halo, ($C_1$-$C_4$ alkyl)—O—, ($C_1$-$C_4$ alkyl)-S(O)$_p$—, where p is 0, 1, or 2; $R^{12}$ is $C_3$-$C_8$ cycloalkyl or a bicycloalkyl group of the Formula:

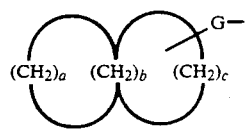

where a and c are independently 1-5, b is 0-5, and (a+c) is greater than 2; Z is a straight or branched $C_4$-$C_{10}$ alkyl, alkenyl, or alkynyl group, ($C_4$-$C_8$ cycloalkyl)-G- optionally substituted with $C_1$-$C_4$ alkyl or phenyl, a bicycloalkyl group of the Formula:

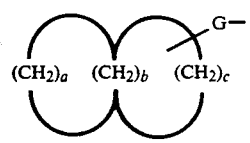

wherein a and c are independently 1-5, b is 0-5, and (a+c) is greater than 2, optionally substituted phen ($C_2$-$C_{10}$) alkyl where the phenyl group can be substituted with $R^{11}$ as previously defined, or -($C_1$-$C_4$ alkylidene)-T-($C_1$-$C_4$ alkyl), where T is —O—, —S—, —SO—, or —SO$_2$—; where each G is independently a bond or $C_1$-$C_4$ alkylidene; or a pharmaceutically-acceptable salt thereof.

Although it is generally proposed that these compounds antagonize central 5-HT1A and 5-HT1B receptors, it has been discovered that these compounds are partial 5-HT1A agonists. As shown below, these compounds are effective inhibitors of gastric acid secretion.

The term "$C_1$-$C_4$ alkyl" refers to methyl, ethyl, propyl, isopropyl, butyl, sec-butyl, t-butyl, and isobutyl. The term "$C_4$-$C_8$ cycloalkyl" refers to cyclobutyl, cyclopentyl, cyclohexyl, cycloheptyl, and cyclooctyl. Optional substituents on the $C_5$-$C_8$ cycloalkyl ring maybe at any position or orientation on the ring other than at the point of attachment to the nitrogen atom.

The term "straight or branched $C_4$-$C_{10}$ alkyl" includes alkyl groups of 4-10 carbon atoms as either straight-chain hydrocarbons or with one or more points of branching. Similarly, the term "straight or branched $C_4$-$C_{10}$ alkenyl or alkynyl group" refers to similar straight or branched hydrocarbon chains containing a double or triple bond, respectively. "Halo" refers to fluoro, chloro, bromo, and iodo.

The term "-($C_1$-$C_4$ alkylidene)-T-($C_1$-$C_4$ alkyl)" refers to two straight or branched $C_1$-$C_4$ alkyl groups bridged by the T functionality. The term "$C_1$-$C_4$ alkylidene" refers to a divalent radical derived from a $C_1$-$C_4$ alkane.

The bicycloalkyl groups defined as part of the $R^{12}$ and Z substituents include bicyclic rings of four to seventeen carbon atoms. These bicycloalkyl groups include bridged and fused two-ring systems.

The $R^{10}$ optional methyl group is one wherein the three-carbon bridge between the aryloxy and amine functionalities are optionally substituted with a methyl group. That is, in addition to the —CH$_2$CH(OH)CH$_2$— bridge as drawn in Formula III, such bridging groups also include —CH(CH$_2$)CH(OH)CH$_2$—, —CH$_2$C(OH)(CH$_3$)CH$_2$—, and —CH$_2$CH(OH)CH(CH$_3$)—.

It is recognized that depending upon the $R^{10}$, hydroxy, and Z substituent groups, one or more stereoisomers and/or enantiomers are possible. This invention is not limited to any particular isomer but includes all possible individual isomers and all combinations thereof.

. The pharmaceutically acceptable addition salts employed in this invention include salts derived from inorganic acids such as hydrochloric acid, nitric acid, phosphoric acid, sulfuric acid, hydrobromic acid, hydriodic acid, phosphorus acid, and the like, as well as salts derived from organic acids, such as aliphatic mono- or di-carboxylic acids, phenyl-substituted alkanoic acids, hydroxy-alkanoic and -alkandioic acids, aromatic acids, aliphatic and aromatic sulfonic acids, and the like.

Most preferred aryloxypropanolamines are represented by the Formula IIIB.

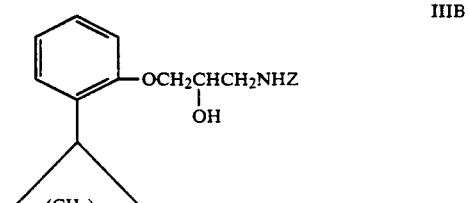

where m is 0-3, especially 2, and Z is ($C_6$-$C_8$ cycloalkyl)-G-, $C_6$-$C_{10}$ alkyl, phenyl ($C_2$-$C_{10}$) alkyl, -($C_1$-$C_4$ alkylidene)-T-($C_1$-$C_4$ alkyl), or

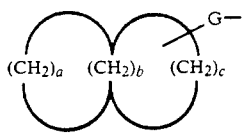

where unless otherwise stated, the variables are as previously defined, or a pharmaceutically acceptable salt thereof.

The compounds employed in the method of this invention are known in the art or can be prepared by methods known in the art. A reference illustrative of this chemistry includes U.S. Pat. No. 3,551,493 (penbutolol and derivatives) and EPA 345,056, which are expressly incorporated by reference herein in their entirety.

In general, the compounds are best prepared according to the following Scheme:

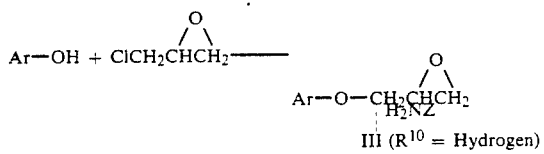

According to this Scheme, the hydroxy aromatic intermediate is reacted with epichlorohydrin or a halo congener thereof to provide the aryloxy-epoxy derivative. This chemistry is well established in the art and can be conducted in a number of ways, generally employing an inert solvent and a nonreactive acid scavenger. The aryloxy-epoxide is then reacted with a primary amine $H_2NZ$ to provide the compounds of Formula III. Once again, the reaction is usually performed in the presence of a nonreactive solvent and at elevated temperatures up to the reflux temperature of the reaction mixture. Scheme I is drawn contemplating those compounds wherein $R^{10}$ is hydrogen; by employing the appropriately substituted epihalohydrin, the other compounds of Formula III may be prepared in a similar manner. The pharmaceutically acceptable salts of Formula III compounds are also be prepared by standard methods known to those skilled in this art.

PREPARATION EXAMPLE 15

1-(2-cyclopeutylphenoxy)-3-(cyclohexylamino)-2-propanol ethanedioate

A mixture of 3.17 g of 3-(2-cyclopentylphenoxy)-1,2-epoxypropane and 2.01 g of cyclohexylamine were heated to reflux in methanol overnight. The mixture was cooled, concentrated in vacuo, diluted with ethyl acetate and treated with a solution of oxalic acid in ethyl acetate. The resulting precipitate was recovered by filtration and crystallized from ethyl acetate/diethyl ether to afford 77% yield of the title product, m.p. 214°-215° C.

The following compounds are prepared in similar fashion from the appropriate aryloxyepoxypropane and corresponding amine:

1-(2-Cyclopentylphenoxy)-3-(cycloheptylamino)2-propanol ethanedioate, 47% yield, m.p. 192°-194° C.

1-(2-Cyclopentylphenoxy)-3-(cyclooctylamino)-2-propanol ethanedioate, 10% yield;

1-(2-Cyclopentylphenoxy)-3-(2,2-dimethyl-3-butylamino)-propanol ethanedioate, 9% yield;

1-(2-Cyclopentylphenoxy)-3-(1,1-dimethylbutylamino)-2-propanol ethanedioate, 21% yield;

1-(2-Cyclopentylphenoxy)-3-(myrtanylamino)-2-propanol ethanedioate;

1-(2-Cyclopentylphenoxy)-3-(Cyclopentylamino)-2-propanol ethanedioate;

1-(2-cyclohexylphenoxy)-3-(tert-butylamino)-2-propanol ethandioate.

Benzodioxanes

A fifth class of direct acing 5-HT1A agonists comprises benzodioxane analogues having the Formula

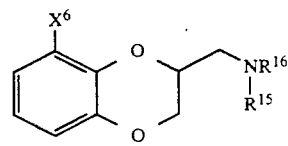

where
$X^6$ is hydrogen, hydroxy, or —O($C_1$-$C_3$)alkyl;
$R^{15}$ is hydrogen; and
$R^{16}$ is —($CH_2$)$_d$—$Y^2$-$Z^1$ where d is 2-4;
$Y^2$ is a bond, —O— or —S—; and
$Z^1$ is unsubstituted, mono- or disubstituted phenyl where the substituents are selected from halo, trifluoromethyl, $C_1$-$C_3$ alkyl, $C_1$-$C_3$ alkoxy, or $C_1$-$C_3$ alkylthio; $C_3$-$C_6$ cycloalkyl group or a 8-azaspiro[4,5]-decan-7,9-dione group; or $N^{15}R^{16}$ comprises a 8-(1-phenyl-1,3,8-triazaspiro[4,5]decan-4-one) group; or a pharmaceutically acceptable salt thereof. Specific examples of members of this class include 2-(2,6-dimethoxyphenoxyethyl)aminomethyl-1,4-benzodioxane, spiroxatrine; 2-[(3-Cyclohexylpropyl)-aminomethyl]-8-hydroxy-1,4-benzodioxane; 2-[2-(3,4-dimethoxyphenyl)ethyl]aminomethyl-1,4-benzodioxane; -[(2-phenylethyl)aminomethyl]-8-ethoxy-1,4-benzodioxane; 2-[(2-phenylethyl)aminomethyl]-1,4-benzodioxane; 4-oxo-1-phenyl-8-(1,4-benzodioxan-2-ylmethyl)-1,3,8-triazaspiro[4.5]decane; and 8-[4-(1,4-benzodioxan-2-ylmethylamino)butyl]-8-azaspiro[4.5]decane-7,9-dione.

In the above Formula IV, the term "halo" means any of fluoro, chloro, bromo and iodo. The term "$C_1$-$C_3$ alkyl" by itself or as part of an alkoxy or alkylthio group means methyl, ethyl, n-propyl, and isopropyl.

As mentioned hereinabove, useful compounds for practicing the method of the present invention includes pharmaceutically acceptable salts of the compounds defined by the above Formula IV Since these compounds are amines, they are basic in nature and accordingly react with any of a number of inorganic and organic acids to form pharmaceutically acceptable acid addition salts. Since the free amines of these compounds are typically oils at room temperature, it is preferable to convert the free amines to their corresponding pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, madelate, and the like. Preferred pharmaceutically acceptable acid addition salts are those formed with mineral acids such as hydrochloric acid and hydrobromic acid, and those formed with organic acids such as maleic acid.

In addition, some of these salts may form solvates with water or organic solvents such as ethanol. Such solvates also are included within the scope of this invention.

These compounds are prepared by alkylation of the appropriate amine with the corresponding halomethylbenzodioxane according to the following reaction:

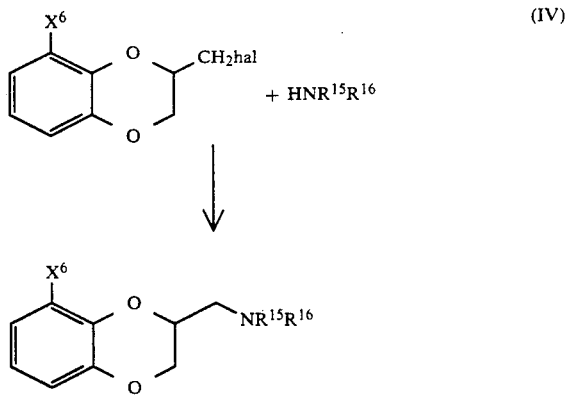

Further details regarding preparation of the benzodioxanes of Formula IV, including preparation of the halomethylbenzodioxanes reactant are described in U.S. Pat. Nos. 2,906,757 and 2,922,744 both of which are incorporated herein by reference in their entirety. When $X^6$ is hydrogen, 2-hydroxymethyl-1,4-benzodioxane can be used to prepare the corresponding halomethyl reactant by procedures well known to those skilled in the art. The 2-hydroxymethyl-1,4-benzodioxane compound is commercially available from Aldrich Chemical Co.

Alternatively, for those compounds where $X^6$ is hydrogen J. Med. Chem., 20, 880 (1977) discloses a method for the synthesis of either 2-tosyloxymethyl enantiomers. This compound is then converted to the primary 2-aminomethyl compound using conditions substantially similar to those described in J. Med. Chem., 8, 446 (1965) for the corresponding bromide. Both of these J. Med. Chem. articles are incorporated by reference herein in their entirety.

Those compounds where $R^{16}$ is $-(CH_2)_d-Y^2-Z^1$ where d is 2-4, $Y^2$ is a bond and $Z^1$ is 8-azaspiro[4,5]-decan-7,9-dione group are prepared according to procedures described in EPA 170,213 and Hibert et. al., J. Med. Chem., 31, 1087-1093 (1988) which are both incorporated by reference herein in their entirety.

The amino reactant to the extent not commercially available, is prepared from commercially available materials using known procedures.

The pharmaceutically acceptable salts of the compounds of Formula IV are prepared using procedures well known to those skilled in the art.

Phenylcyclopropylamines

A sixth class of direct acting 5-HT1A agonists comprises 2-phenyl-N,N-dialkylcyclopropylamines having the Formula

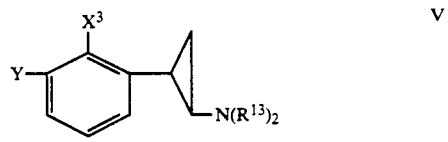

where
$R^{13}$ is $C_1-C_3$ alkyl;
$X^3$ is hydrogen, OH or $OCH_3$;
Y is hydrogen, OH or $OCH_3$; and pharmaceutically acceptable salts thereof provided that one of $X^3$ and Y must be hydrogen.

It is recognized that these compounds exist in two enantiomeric forms. This invention is not limited to any particular isomer, but includes both individual enantiomers and mixtures thereof.

As mentioned above, useful compounds for practicing the method of the present invention includes pharmaceutically acceptable salts of the compounds defined by the above Formula. Since these are amines, they are basic in nature and accordingly react with any of a number of inorganic and organic acids to form pharmaceutically acceptable acid addition salts. Acids commonly employed to form such salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, madelate, and the like. Preferred pharmaceutically acceptable acid addition salts are those formed with mineral acids such as hydrochloric acid and hydrobromic acid, and those formed with organic acids such as maleic acid.

In addition, some of these salts may form solvates with water or organic solvents such as ethanol. Such solvates also are included within the scope of this invention.

Representative examples of these compounds includes:

2-(2-hydroxyphenyl)-N,N-di-n-propyl-cyclopropylamine;

2-(3-hydroxyphenyl)-N,N-di-n-propyl-cyclopropylamine;

2-(2-methoxyphenyl)-N,N-di-n-propyl-cyclopropylamine;

2-(3-methoxyphenyl)-N,N-di-n-propyl-cyclopropylamine;

2-(2-hydroxyphenyl)-N,N-diethyl-cyclopropylamine;

2-(3-hydroxyphenyl)-N,N-diethyl-cyclopropylamine;

2-(2-methoxyphenyl)-N,N-diethyl-cyclopropylamine;

2-(3-methoxyphenyl)-N,N-diethyl-cyclopropylamine;

2-(2-hydroxyphenyl)-N,N-dimethyl-cyclopropylamine; and 2-(3-hydroxyphenyl)-N,N-dimethly-cycloproplyamine.

The 2-(phenyl)-N.N-dialkylcyclopropylamines of the above Formula V are prepared according to procedures described in Arvidsson et. al., *J. Med. Chem.*, 31, 92–99 (1988) which is incorporated by reference herein in its entirety.

The optically active isomers of the reacemates of the compounds of Formula IV are also considered within the scope of compounds useful in providing the method of the present invention. Such optically active isomers are prepared from their respective optically active precursors by the procedures described in Arvidsson et. at., *J. Med. Chem* , 31, 92–99 (1988), or by resolving the racemic mixtures. It is believed this resolution can be carried out in the presence of a resolving agent, by chromatography or by repeated crystallization. Useful resolving agents include d- and l-tartaric acids, d- and l-ditoluoyltartaric acids, and the like.

The compounds employed as initial starting materials in the synthesis of the compounds of this invention are well known and commercially available or readily synthesized by standard procedures commonly employed by those of ordinary skill in the art.

The pharmaceutically acceptable acid addition salts are typically formed by reacting a 2-(phenyl)-N,N-dialkyl-cyclopropylamine of Formula V with an equimolar or excess amount of acid. The reactants are generally combined in a mutual solvent such as diethyl ether or benzene, and the salt normally precipitates out of solution within about one hour to 10 days, and can be isolated by filtration.

N-Arylpiperazines

A seventh class of direct acting 5-HT1A agonists comprises N-arylpiperazine derivates or a pharmaceutically acceptable salt thereof. Representative examples of compounds within this class include those disclosed in U.S. Pat. No. 4,818,756, which describes substituted 2-pyrimidinyl-1-piperazine derivatives and defines those derivatives with greater particularly. U.S. Pat. No. 4,818,756, which is incorporated by reference herein in its entirety, also discloses methods for preparing those compounds.

Further examples of compounds within this class include those disclosed in EPA 082 402 which describes succinimide derivatives substituted with piperazinylalkyl group at the imido nitrogen atom. EPA 082 402, which is incorporated by reference herein in its entirety, discloses methods for preparing those compounds.

Still further examples of 5-HT1A agonist compounds within this class are disclosed in *J. Med. Chem.*, 15, 477 (1972); *J. Med. Chem.*, 26, 194 (1983); and *J. Med. Chem.*, 31, 1382 (1988) which are all incorporated by reference herein in their entirety. These three references also describe methods for preparing those compounds.

The N-arylpiperazines may be further substituted by a 8-azospiro[4,5]decane-7 9-dione; 4,4-dimethyl-2,6-piperidinedione; benzisothiazole-3(2H)-one-1,1-dioxide; 3aα, 4a, 5, 6, 7aα-hexahydro-4, 7-methano-1H-isoindole-1,3(2H)-dione; phenyl, substituted phenyl where the substituents are selected from halogen, $C_1$–$C_4$ alkyl, $C_1$–$C_4$ alkoxy, amino, acetamido, 2-haloacetamido, and trifluoromethyl, where said further substituent is bonded to the other nitrogen atom of the N-arylpiperazine by a $C_1$–$C_4$ alkylene bridge.

As used for this class of compounds, "halogen" and "halo" should be understood as chloro, bromo, fluoro, and iodo.

The N-arylpiperazines described in the above references and within the scope of the present invention are 5-HT1A agonists having the Formula:

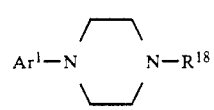

VI where

Ar$^1$ is 2-pyrimidinyl; phenyl or substituted phenyl where the substituent is selected from halo: $C_1$–$C_4$ alkyl, $C_1$–$C_4$ alkoxy, and $CF_3$;

R$^{18}$ is hydrogen or —(CH$_2$)$_q$—Ar$^2$ where q is 1 to 4; and

Ar$^2$ is phenyl, substituted phenyl where the substituent is selected from halo, $C_1$–$C_4$ alkyl, $C_1$–$C_4$ alkoxy, $NH_2$, $NHC(O)CH_3$, $NHC(O)CH_2Cl$ or $CF_3$; or Ar$^2$ is a group selected from groups having the Formulae:

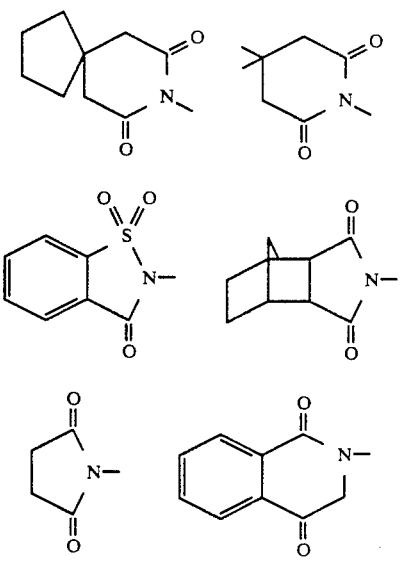

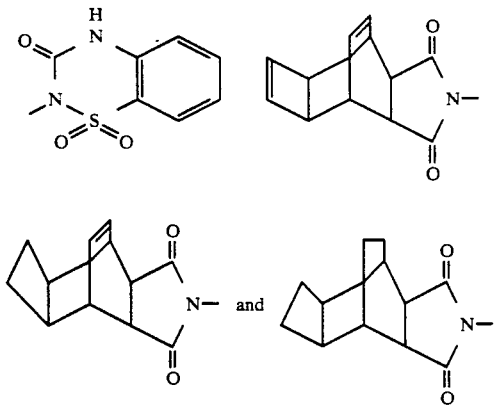

or a pharmaceutically acceptable salt thereof.

As mentioned above, useful compounds for practicing the method of the present invention includes pharmaceutically acceptable acid addition salts of the arylpiperazines compounds. Since these compounds are amines, they are basic in nature and accordingly react with any of a number of inorganic and organic acids to form pharmaceutically acceptable acid addition salts. Acids commonly employed to form such salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid and citric acid.

In addition, some of these salts may form solvates with water or organic solvents such as ethanol. Such solvates also are included within the scope of this invention.

Representative examples of these compounds includes 8-[4-[4-(2-pyrimidinyl)-1-piperazinyl]butyl]8-azaspiro[4.5]decane-7,9-dione (buspirone); 4,4-di-methyl-1-[4-[4-(2-pyrimidinyl)-1-piperazinyl]butyl]-2,6-piperidinedione (gepirone); 2-[4-[4-(2-pyrimidinyl)-1-piperazinyl]butyl]benzisothiazole-3(2H)-one 1,1-dioxide (ipsapirone); 1-(3-trifluoromethylphenyl)piperazine; 1-(3-trifluoromethylphenyl)-4-[2-(4-aminophenyl)ethyl]-piperazine (PAPP); 1-(3-trifluoromethylphenyl)-4-[2-[3-(2-bromoacetamido)phenyl]ethyl]piperazine; 1-(3-tri-fluoromethylphenyl)-4-[2-[3-(2-chloroacetamido)phenyl-ethyl]piperazine; and (3aα, 4α, 5, 6, 7α, 7aα)-hexa-hydro-2-[4-4-(2-pyrimidinyl)-1-piperazinyl]butyl]-4,7-methano-1H-isoindole-1,3(2H)-dione.

The N-arylpiperazine compounds are prepared by procedures described in U.S. Pat. No. 4,518,756 and EPA 082 402, which have both been incorporated by reference herein, or other procedures well-known to those of ordinary skill in the art.

For example, 8-[4-[4-(2-pyrimidinyl)-1-piperazinyl]-butyl]-8-azaspiro[4,5]decane is prepared by the condensation of 1-(2-pyrimidinyl)piperazine with 3-chloro-1-cyanopropane by means of $Na_2CO_3$ in n-butanol gives 4-(2-pyrimidinyl)-1-(3-cyanopropyl)piperazine which is redued with $LiAlH_4$ or with $H_2$ and Raney nickel (RaNi) yielding 4-(2-pyrimidinyl)-1-(4-aminobutyl)piperazine, which is finally condensed with 8-oxaspiro [4,5]-decane-7,9-dione (3,3-tetramethyleneglutaric anhydride) in pyridine.

The preparation of 4,4-dimethyl-1-[4-[4-(2-pyrimidinyl)-1-piperazinyl]butyl]-2,6-piperidinedione proceeds by preparing the quaternary salt from 1-(pyrimidin-2-yl)piperazine and 1,4-dibromobutane which then undergoes reaction with 3,3-dimethyl-glutarimide in the presence of potassium carbonate in refluxing xylene to afford the free base which is isolated by acid extraction and basification of the extract. Treatment of the free base with HCI in isopropanol affords the compound as the monohydrochloride salt.

The compound 2-[4-[4-(2-pyrimidinyl)piperazinyl]-butyl]benzoisothiazole-3(2H)-one 1,1-dioxide is prepared by the reaction of benzoisothiazole-3(2H)-one 1,1-dioxide with 1,4-dibromobutane by means of NaH in DMF to afford 2-(4-bromobutyl)benzoisothiazole-3(2H)-one 1,1-dioxide which is then condensed with 1-(2-pyrimidinyl)piperazine by means of $K_2CO_3$ in refluxing chlorobenzene.

The compound 3aα,4α,5,6,7α,7aα)-hexahydro-2-[4-[4-(2-pyrimidinyl)-1-piperazinyl]butyl]-4,7-methano-1H-isoindole-1,3(2H)-dione prepared by the condensation of norbornane-2,3-di-endocarboxylic anhydride with 1-(4-aminobutyl)-4-(2-pyrimidinyl)piperazine in refluxing pyridine.

Starting materials for these preparations, to the extent not commercially available are prepared by methods well known to those skilled in the art.

Further preparation information on the N-arylpiperazines is set forth in Yevich et. al., *J. Med. Chem.*, 26, (2), 194–203 (1983); Wu et al., *J. Med. Chem.*, 15, (5), 477–479 (1972); and Wu et al., *J. Med. Chem.*, 12, 876–881 (1969) which are incorporated by reference herein in their entirety.

Piperidinylmethyl Tetrahydroisoquinolines

An eighth class of direct acting 5-HT1A agonists comprises 2-(4-piperidinylmethyl)-1,2,3,4-tetrahydroisoquinolines having the Formula:

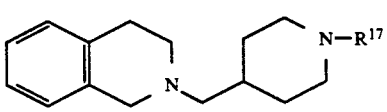

VII where $R^{17}$ is hydrogen; $C_1$–$C_6$ alkyl; allyl; ($C_3$–$C_6$ cycloalkyl)methyl; benzyl where the ring is optionally substituted with 1, 2, or 3 substituents selected from halo. $CF_3$, $NO_2$, $NH_2$, $N(CH_3)_2$, $CN$, $CONH_2$, $C_1$–$C_3$ alkyl, C$_1$-C$_3$ alkoxy and C$_1$-C$_3$ alkylthio; 2-phenylethyl; 3-phenylpropyl; 3-phenylpropen-2-yl; phenylcarbonylmethyl; naphthylmethyl; pyridylmethyl; furanylmethyl; thienylmethyl; CF$_3$CO; phenylcarbonyl optionally ring substituted with 1, 2, or 3 substituents selected from halo, NO$_2$, CF$_3$, C$_1$-C$_3$ alkyl, C$_1$-C$_3$ alkoxy and C$_1$-C$_3$ alkylthio; 1-oxo-3-phenylpropen-2-yl; naphthylcarbonyl; pyridinylcarbonyl; furancarbonyl; thienylcarbonyl; or 2- or 5-indolylcarbonyl or a pharmaceutically acceptable salt thereof.

This class of compounds and methods for their preparation are disclosed in EPA 306375 which is incorporated by reference herein in its entirety.

As used for this eighth class of compounds "alkyl" by itself or as part of another moiety means, unless otherwise stated a straight or branched chain group having the stated number of carbon atoms. Representative examples include methyl, ehtyl, n-propyl, isopropyl and higher homologs and isomers where stated. "Halo" means fluoro, chloro, bromo or iodo.

As mentioned above, useful compounds for practicing the method of the present invention includes pharmaceutically acceptable salts of the compounds. Since these compounds are amines, they are basic in nature and accordingly react with any of a number of inorganic and organic acids to form pharmaceutically acceptable acid addition salts. Acids commonly employed to form such salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexynel, 6-dioate, benzoate, chlorobenzoate, methylbenzoate, dinitrobenzohydroxybenzoate, methoxybenzoate, phthalate, sulfonate, xylenesulfonate, phenylacetate, phenylpropionate, phenylbutyrate, citrate, lactate, $\gamma$-hydroxybutyrate, glycollate, tartrate, methanesulfonate, propanesulfonate, naphthalene-1-sulfonate, naphthalene-2-sulfonate, madelate, and the like. Preferred pharmaceutically acceptable acid addition salts are those formed with mineral acids such as hydrochloric acid and hydrobromic acid, and those formed with organic acids such as maleic acid.

In addition, some of these salts may form solvates with water or organic solvents such as ethanol. Such solvates also are included within the scope of this invention.

The present invention provides a method of inhibiting gastric acid secretion in mammals, preferably humans, comprising administering to a mammal in need of of gastric acid secretion inhibition an effective dose of a direct acting 5-HT1A receptor agonist, or a pharmaceutically acceptable salt thereof.

By the term "effective dose" is meant an amount of a 5-HT1A agonist, or a pharmaceutically acceptable salt thereof, which will inhibit from about one percent to about 99 percent of the volume of gastric acid secreted or inhibit the acidity of gastric secretion by a pH value of from about 0.1 to about 5.0, or inhibit both the volume and acidity of gastric secretion within said parameters. The gastric acid secretion inhibition contemplated by the present method includes both medical therapeutic and/or prophylactic treatment, as appropriate. The specific dose of a particular compound, or pharmaceutically acceptable salt thereof, administered according to this invention will, of course, be determined by the particular circumstances surrounding the case, including, for example, the compound administered, the route of administration, and the condition being treated. A typical daily dose will generally contain from about 0.01 mg/kg to about 20 mg/kg of a direct acting 5-HT1A agonist or a pharmaceutically acceptable salt thereof. Preferred daily doses generally will be from about 0.05 to about 10 mg/kg and more preferrably from about 0.1 to about 5 mg/kg.

The compounds useful in practicing the method of this invention are preferably formulated prior to administration. Such a pharmaceutical formulation comprises a 5-HT1A against compound or a pharmaceutically acceptable salt thereof and a pharmaceutically acceptable carrier, diluent or excipient therefor.

The active ingredient in such formulations comprises from about 0.1% to about 99% by weight of the formlation. By "pharmaceutically acceptable" is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methylhydroxybenzoates, propyl hydroxybenzoates, talc, magnesium stearate, and mineral oil. The formulations may additionally include lubricating agents, wetting agents, emulsifying agents, suspending agents, preserving agents, sweetening agents, flavoring agents, and the like. The compositions of the invention may be formulated so as to provide quick, sustained or delayed release of the active ingredient after administration to the patient by employing procedures well known in the art.

The compositions are preferably formulated in a unit dosage form, each dosage generally containing from about 0.1 to about 500 mg, and preferably from about 1 to about 250 mg, of the active ingredient. The term "unit dosage form" refers to physically discrete units suitable as unitary dosages for human subjects and other mammals, each unit containing a predetermined quantity of active material calculated to produce the desired therapeutic and/or prophylactic effect, in association with a suitable pharmaceutical carrier.

The following formulation examples are illustrative only and are not intended to limit the scope of the invention in any way. "Active ingredient", of course, means a direct acting 5-HT1A agonist or a pharmaceutically acceptable salt thereof as described herein.

Formulation 1

Hard gelatin capsules are prepared using the following ingredients:

|  | Quantity (mg/capsule) |
|---|---|
| Active ingredient | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
|---|---|
| Active Ingredient | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

|  | Weight % |
|---|---|
| Active Ingredient | 0.25 |
| ethanol | 29.75 |
| Propellant 22 (chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
|---|---|
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |

| -continued | |
|---|---|
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 60 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
|---|---|
| starch | 59 mg |
| microcrystalline cellulose | 59 mg |
| magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
|---|---|
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| isotonic saline | 1000 ml |

The solution of the above ingredients generally is administered intravenously at a rate of 1 ml per minute to a subject in need of the inhibition of gastric acid secretion.

The gastric acid inhibition activity of direct acting 5-HT1A agonists was established by evaluations using the pylorus ligated rat model. In the pylorus ligated rat model, changes in basal acid secretion may reflect a stimulatory or inhibitory action depending on treatment of compound type tested. The compounds tested were confirmed by various receptor binding tests to have an affinity for the 5-HT1A receptor prior to testing in the pylorus ligated rat model.

The pylorus ligated rat model used is a modification of the procedure developed by Shay (Shay, H., Komarov, A. A. and Greenstein, M.: "Effects of vagotomy in the rat." *Arch. Surg.* 49:210–226, 1949). Male Sprague-Dawley rats weighing approximately 200 g were starved 24 hours prior to using, with water allowed ad libitum. Under light ether anesthetic the pylorus is ligated, simultaneously the rat is dosed intraperitoneally (i.p.) or subcutaneously (s.c.) and allowed 2 hours for stomach acid accumulation. At the end of 2 hours the rats are sacrificed. Stomach content is measured and titrated to a pH end point of 7.0. Each experiment has its own control group for determining percent of acid change over the 2-hour time period.

Specific compounds within the scope of the above general classes of direct acting 5-HT1A agonists were tested. For evaluation purposes, the compound to be tested is dissolved in distilled water, or in 10% dimethyl sulfoxide, depending upon its solubility. The results of these evaluations are set forth below in Tables I through VI. All compounds were dosed intraperitoneally, unless otherwise indicated.

TABLE I

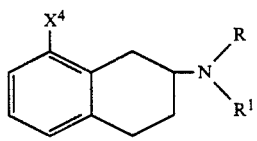

| Evaluation Example No. | $X^4$ | R and $R^1$ | Dose μmoles/kg | Percent Inhibition |
|---|---|---|---|---|
| 1 | OMe | Pr | 10 | 96.4 ± 0.7 |
| 2 | SMe | Pr | 10 | 94.9 ± 1.2 (+) isomer |
| 3 | SMe | Pr | 10 | 89.8 ± 4.9 (−) isomer |
| 4 | $CONH_2$ | Pr | 10 | 82.5 ± 7.4 |
| 5 | SMe | Me | 10 | 80.7 ± 8.4 |
| 6 | Br | Pr | 10 | 39.6 ± 10.9 |
| 7 | F | Pr | 10 | 24.6 ± 7.9 |
| 8 | OH | Pr | 2.0 | 80.1 ± 6.3 |

TABLE II

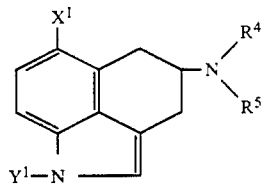

| Evaluation Example No. | $X^1$ | $R^4$ and $R^5$ | $Y^1$ | Dose μmoles/kg | Percent Inhibition |
|---|---|---|---|---|---|
| 9 | CN | Pr | H | 10 | 92.2 ± 3.2 |
| 10 | CN | Me | H | 10 | 91.6 ± 3.9 |
| 11 | $NO_2$ | Pr | H | 10 | 89.8 ± 1.4 |
| 12 | Br | Pr | H | 10 | 87.0 ± 1.8 |
| 13 | $CO_2Me$ | Pr | H | 2.0 | 86.4 ± 2.5 |
| 14 | OMe | Pr | H | 10 | 86.4 ± 4.0 |
| 15 | $CO_2H$ | Pr | H | 10 | 81.7 ± 5.8 |
| 16 | OMe | Pr | iPr | 10 | 80.9 ± 5.5 |
| 17 | CHO | Me | H | 2.0 | 79.2 ± 4.6 |
| 18 | $CONH_2$ | Pr | H | 10 | 65.5 ± 7.1 |

TABLE III

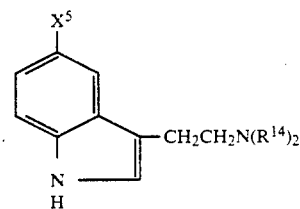

| Evaluation Example No. | $X^5$ | $R^{14}$ | Dose μmoles/kg | Percent Inhibition |
|---|---|---|---|---|
| 19 | $CONH_2$ | Pr | 10 | 92.7 ± 3.3 |

TABLE IV

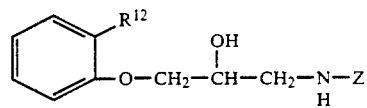

| Evaluation Example No. | $R^{12}$ | Z | Dose μmoles/kg | Percent Inhibition |
|---|---|---|---|---|
| 20 | cyclopentyl | (norbornyl structure) | 10 | 72.4 ± 7.5 |
| 21 | cyclopentyl | cyclooctyl | 10 | 65.1 ± 5.7 |
| 22 | cyclohexyl | —C(CH_3)_3 | 10 | 30.8 ± 12.3 |
| 23 | cyclopentyl | —C(CH_3)_2CH_2CH_2CH_3 | 10 | 26.4 ± 15.4 |
| 24 | cyclopentyl | cyclopentyl | 10 | 19.7 ± 14.8 |

TABLE V

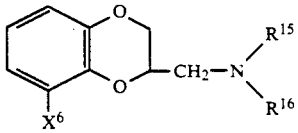

| Evaluation Example No. | X⁶ | R¹⁶ | R¹⁵ | Dose μmoles/kg | Percent Inhibition |
|---|---|---|---|---|---|
| 25 | OH | —(CH₂)₃-cyclohexyl | H | 10 | 70.4 ± 8.4 |
| 26 | H | —(CH₂)₂—C₆H₃(OCH₃)₂ | H | 10 | 58.9 ± 6.6 |
| 27 | OEt | —(CH₂)₂—C₆H₅ | H | 10 | 38.3 ± 15.9 |
| 28 | H | 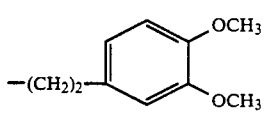 | | 10 | 29.3 ± 10.0 (—) isomer |
| 29 | H | 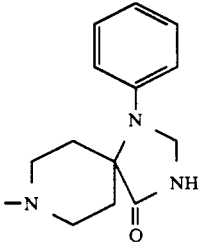 | | 10 | 24.6 ± 9.2 (+) isomer |
| 30 | H | —(CH₂)₂—C₆H₅ | H | 10 | 0.3 ± 14.1 |

TABLE VI

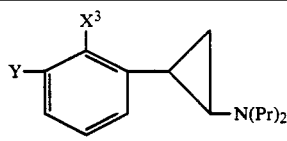

| Evaluation Example No. | X³ | Y | μmoles/kg | Inhibition |
|---|---|---|---|---|
| 31 | H | OH | 10 | 48.2 ± 17.5 |
| 32 | OH | H | 10 | 22.6 ± 11.8 |

TABLE VII

| Evaluation Example No. | Dose | ED₅₀ μmoles/kg |
|---|---|---|
| 1 | i.p. | 1.54 |
| 2 | i.p. | 1.56 |
| 3 | i.p. | 1.42 |
| 8 | i.p. | 1.56 |
| 8 | s.c. | 0.46 |
| 13 | i.p. | <0.10 |
| 14 | i.p. | <0.10 |
| 15 | i.p. | 1.00 |
| 17 | i.p. | 1.26 |
| 33 (buspirone) | s.c. | 4.19 |
| Standard (5-HT) | i.p. | 11.50 |

As a standard serotonin (5-HT) was also evaluated in the pylorus ligated rat model. At a dose of 20 micromoles/kg, 5-HT demonstrated 56.1 percent, plus or minus 9.7, inhibition of gastric acid secretion.

The ED₅₀ values for certain specific compounds were estimated based on data from the pylorus ligated rat model evaluations. These results are set forth below in Table VII. Under "Dose", i.p. means intraperitoneally and s.c. means subcutaneously.

We claim:

1. A method of inhibiting gastric acid section in mammals comprising administering to a mammal in need of gastric acid secretion inhibition a gastric acid secretion inhibiting dose of a direct acting 5-HT1A agonist which is a piperidinylmethyl tetrahydroisoquinoline or a pharmaceutically acceptable acid addition salt thereof.

2. The method according to claim 1 wherein said mammals are humans.

3. The method according to claim 1 wherein said piperidinylmethyl tetrahydroisoquinoline has the Formula:

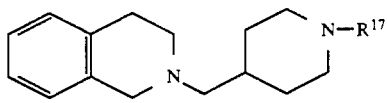

VI where
R$^{17}$ is hydrogen; C$_1$-C$_6$ alkyl; allyl; (C$_3$-C$_6$ cycloalkyl)methyl; benzyl where the ring is optionally substituted with 1, 2, or 3 substituents selected from halo, CF$_3$, NO$_2$, NH$_2$, N(CH$_3$)$_2$, CN, CONH$_2$, C$_1$-C$_3$ alkyl, C$_1$-C$_3$ alkoxy and C$_1$-C$_3$ alkylthio; 2-phenylethyl; 3-phenylpropyl; 3-phenylprop-2-enyl; phenylcarbonylmethyl; naphthylmethyl; pyridylmethyl; furanylmethyl; thienyln methyl; C$_2$-C$_6$ alkanoyl; C$_3$-C$_6$ cycloalkylcarbonyl; CF$_3$CO; phenylcarbonyl optionally ring substituted with 1, 2, or 3 substituents selected from halo, NO$_2$, CF$_3$, C$_1$-C$_3$ alkyl, C$_1$-C$_3$ alkoxy and C$_1$-C$_3$ alkylthio; 1-oxo-3-phenylprop-2-enyl; naphthylcarbonyl; pyridinylcarbonyl; furancarbonyl; thienylcarbonyl; or 2- or 5-indolylcarbonyl or a pharmaceutically acceptable salt thereof.

4. The method according to claim 3 where R$^{17}$ is C$_1$-C$_3$ alkyl; allyl; (C$_3$-C$_6$ cycloalkyl)methyl; benzyl where the ring is optionally substituted with 1,2, or 3 substituents selected from halo, CF$_3$, NO$_2$, NH$_2$, N(CH$_3$)$_2$, CN, CONH$_2$, C$_1$-C$_3$ alkyl, C$_1$-C$_3$ alkoxy and C$_1$-C$_3$ alkylthio; 2-phenylethyl; 3-phenylpropyl; 3-phenylprop-2-enyl; phenylcarbonylmethyl; naphthylmethyl; pyridylmethyl; furanylmethyl; or thienylmethyl or a pharmaceutically acceptable salt thereof.

* * * * *